(12) United States Patent
Ward et al.

(10) Patent No.: US 7,671,162 B2
(45) Date of Patent: Mar. 2, 2010

(54) CONTROL OF POLYMER SURFACE MOLECULAR ARCHITECTURE VIA AMPHIPATHIC ENDGROUPS

(75) Inventors: Robert S. Ward, Lafayette, CA (US); Keith R. McCrea, Concord, CA (US); Yuan Tian, Alameda, CA (US); James P. Parakka, San Bruno, CA (US)

(73) Assignee: DSM IP Assets B.V., Heerlen (NL)

( * ) Notice: Subject to any disclaimer, the term of this patent is extended or adjusted under 35 U.S.C. 154(b) by 1031 days.

(21) Appl. No.: 11/211,734

(22) Filed: Aug. 26, 2005

(65) Prior Publication Data

US 2005/0282997 A1 Dec. 22, 2005

Related U.S. Application Data

(63) Continuation-in-part of application No. 11/125,196, filed on May 10, 2005, now abandoned, which is a continuation of application No. PCT/US03/35912, filed on Nov. 12, 2003.

(60) Provisional application No. 60/425,253, filed on Nov. 12, 2002.

(51) Int. Cl.
*C08G 18/00* (2006.01)
*C08G 77/04* (2006.01)
*C08G 77/22* (2006.01)

(52) U.S. Cl. .............................. 528/44; 528/10; 528/25; 528/28; 528/34; 525/453; 525/459; 525/460

(58) Field of Classification Search .................. 623/1.1; 528/44

See application file for complete search history.

(56) References Cited

U.S. PATENT DOCUMENTS 4,663,413 A * 5/1987 Ward et al. .................... 528/26

(Continued)

FOREIGN PATENT DOCUMENTS

WO WO-95/26993 A1 10/1995

(Continued)

OTHER PUBLICATIONS

Chen et al., "Detection of Hydrophobic End Groups on Polymer Surfaces by Sum-Frequency Generation Vibrational Spectroscopy", *J. Am. Chem. Soc.*, vol. 122, No. 43, pp. 10615-10620 (2000).

*Primary Examiner*—Randy Gulakowski
*Assistant Examiner*—Robert Loewe
(74) *Attorney, Agent, or Firm*—Birch, Stewart, Kolasch & Birch, LLP

(57) ABSTRACT

Polymers whose surfaces are modified by endgroups that include amphipathic surface-modifying moieties. An amphipathic endgroup of a polymer molecule is an endgroup that contains at least two moieties of significantly differing composition, such that the amphipathic endgroup spontaneously rearranges its positioning in a polymer body to position the moiety on the surface of the body, depending upon the composition of the medium with which the body is in contact, when that re-positioning causes a reduction in interfacial energy. An example of an amphipathic surface-modifying endgroup is one that has both a hydrophobic moiety and a hydrophilic moiety in a single endgroup. For instance, a hydrophilic poly(ethylene oxide) terminated with a hydrophilic hydroxyl group is not surface active in air when the surface-modifying endgroup is bonded to a more hydrophobic base polymer. If the hydroxyl group on the oligomeric poly(ethylene oxide) is replaced by a hydrophobic methoxy ether terminus, the poly(ethylene oxide) becomes surface active in air, and allows the poly(ethylene oxide) groups to crystallize in the air-facing surface. In this example, immersion in water destroys the crystallinity as the poly(ethylene oxide) sorbs water and the hydrophobic methoxy group retreats below the surface of the polymer. Also disclosed are methods and articles of manufacture that make use of these polymers.

9 Claims, 8 Drawing Sheets

U.S. PATENT DOCUMENTS

| | | | |
|---|---|---|---|
| 4,675,361 A * | 6/1987 | Ward, Jr. | 525/92 A |
| 4,686,137 A * | 8/1987 | Ward et al. | 442/76 |
| 4,705,709 A * | 11/1987 | Vailancourt | 428/36.91 |
| 4,838,876 A * | 6/1989 | Wong et al. | 604/265 |
| 4,861,830 A * | 8/1989 | Ward, Jr. | 525/92 A |
| 4,963,595 A * | 10/1990 | Ward et al. | 525/415 |
| 5,017,664 A * | 5/1991 | Grasel et al. | 525/454 |
| 5,100,992 A * | 3/1992 | Cohn et al. | 528/26 |
| 5,120,813 A * | 6/1992 | Ward, Jr. | 528/28 |
| 5,235,003 A * | 8/1993 | Ward et al. | 525/476 |
| 5,274,028 A * | 12/1993 | Bertrand et al. | 525/17 |
| 5,428,123 A * | 6/1995 | Ward et al. | 528/28 |
| 5,514,380 A * | 5/1996 | Song et al. | 424/426 |
| 5,589,563 A | 12/1996 | Ward et al. | |
| 6,120,904 A * | 9/2000 | Hostettler et al. | 428/423.3 |
| 6,127,507 A * | 10/2000 | Santerre | 528/66 |
| 6,306,821 B1 * | 10/2001 | Mikos et al. | 514/2 |
| 6,315,788 B1 * | 11/2001 | Roby | 606/230 |
| 2002/0141942 A1 * | 10/2002 | Riffle et al. | 424/9.1 |
| 2003/0162905 A1 * | 8/2003 | Benz et al. | 525/294 |
| 2004/0146715 A1 * | 7/2004 | Guire et al. | 428/412 |
| 2004/0185257 A1 * | 9/2004 | DeGrado et al. | 428/411.1 |
| 2004/0202639 A1 * | 10/2004 | DeGrado et al. | 424/78.22 |
| 2005/0238722 A1 * | 10/2005 | Pathak et al. | 424/486 |
| 2006/0216324 A1 * | 9/2006 | Stucke et al. | 424/422 |

FOREIGN PATENT DOCUMENTS

| | | |
|---|---|---|
| WO | WO-99/47072 A1 | 9/1999 |

* cited by examiner

US 7,671,162 B2

CONTROL OF POLYMER SURFACE MOLECULAR ARCHITECTURE VIA AMPHIPATHIC ENDGROUPS

This application is a continuation-in-part of U.S. patent application Ser. No. 11/125,196, which was filed on May 10, 2005 now abandoned. Ser. No. 11/125,196 is in turn a continuation of international application PCT/US03/35912, filed 12 Nov. 2003. This application claims priority under 35 U.S.C. §120 to Ser. No. 11/125,196 and to PCT/US03/35912. The entire contents of Ser. No. 11/125,196 and of PCT/US03/35912 are hereby expressly incorporated by reference. This application claims priority under 35 U.S.C. §119(e) to U.S. provisional application Ser. No. 60/425,253, filed 12 Nov. 2002. The entire contents of Ser. No. 60/425,253 are likewise hereby expressly incorporated by reference.

FIELD OF THE INVENTION

This invention provides novel methods that enable the configuration of the nanostructure, supramolecular structure, and/or conformation of a molecular monolayer at the surface of a polymer body. This invention also provides novel articles of manufacture that employ the novel methods of the invention to enhance their suitability for use in medical and other applications. Finally, this invention provides novel polymers suitable for making the novel articles of the invention.

BACKGROUND OF THE INVENTION

U.S. Pat. No. 5,589,563 (Robert S. Ward and Kathleen A. White) describes the use of surface modifying endgroups (SMEs) to tailor polymer surface properties. The '563 patent is entitled "SURFACE-MODIFYING ENDGROUPS FOR BIOMEDICAL POLYMERS". The entire contents of U.S. Pat. No. 5,589,563 are hereby expressly incorporated by reference. As documented in the '563 patent, a variety of hydrophobic and hydrophilic endgroups has been demonstrated to enable the achievement of useful changes in surface properties of polymers. Such surface properties include biostability, protein adsorption, abrasion resistance, bacterial adhesion and proliferation, fibroblast adhesion, and coefficient of friction. SME polymers have also been used in low bulk concentration as surface modifying additives (SMAs) to SME-free base polymers.

As explained in U.S. Pat. No. 5,589,563, the surface activity of SMEs is high, in part because of the added mobility of polymer endgroups relative to backbone groups. An endgroup is tethered to the bulk polymer at only one point and is otherwise free to migrate to interfaces. This migration occurs spontaneously if the result is a reduction in system interfacial energy. Thus, hydrophobic groups such as silicone will migrate to air interfaces and hydrophilic groups such as poly (ethylene oxide) will migrate to aqueous interfaces. The surfaces of polymers containing SME endgroups will restructure following a change in their environment.

U.S. Pat. No. 5,589,563 teaches in lines 19-27 of column 8 that, where mixed endgroups are present in a single polymer, complex surface activity may be achieved. Of the specific polymers disclosed in the '563 patent, only those of Examples 6 and 8 may be considered to contain surface-modifying amphipathic moieties, as that terminology is used in the present invention.

SUMMARY OF THE INVENTION

The present invention provides polymers in which the surface behavior of polymers is modified by amphipathic SMEs. An amphipathic endgroup of a polymer molecule is an endgroup that contains at least two moieties of significantly differing composition, such that the amphipathic endgroup spontaneously rearranges its positioning in a polymer body to position the moiety on the surface of the body depending upon the composition of the medium with which the body is in contact, where the positioning causes a reduction in interfacial energy. An example of an amphipathic SME is an SME that has both a hydrophobic and a hydrophilic moiety in a single endgroup. Thus, for instance, a hydrophilic poly(ethylene oxide) terminated with a hydrophilic hydroxyl group is not surface active in air when the SME is bonded to a more hydrophobic base polymer. If the hydroxyl group on the oligomeric poly(ethylene oxide) is replaced by a hydrophobic methoxy ether terminus, the poly(ethylene oxide) becomes surface active in air, even allowing the poly(ethylene oxide) groups to crystallize in the air-facing surface region. Immersion in water destroys the crystallinity as the poly(ethylene oxide) sorbs water and the hydrophobic methoxy group "dives" below the polymer surface.

ANALYTICAL CONSIDERATIONS. Characterizing polymer surfaces that are modified by SMEs requires very surface-sensitive analytical methods. Attenuated total reflection infrared spectroscopy (ATR-IR) is generally not useful, since the region modified by SMEs appears to be the outer few molecular layers, and ATR-IR probes up to hundreds of monolayers below the surface. Methods based on the contact angle of probe liquids have the required surface sensitivity, but do not provide specific information about the chemical nature of the outer monolayer. Sum-frequency generation spectroscopy (SFG) has been found to provide good results. SFG is a laser-based, nonlinear optical technique which, with beam polarization, can also provide information about the orientation of surface chemical groups at solid-gas and solid liquid interfaces. SFG correlates perfectly with contact angle goniometry.

Sum frequency generation is a surface specific vibrational spectroscopy that probes the outermost layer of molecules on a surface. Because SFG utilizes lasers for probing and analysis, the signal to noise ratio is determined by the quality (optical smoothness) of the surface. A rough surface that scatters light decreases the signal-to-noise ratio by scattering the generated SFG light away from the detector in addition to increasing the noise background. SFG analysis is much more efficient on optically smooth surfaces and can decrease acquisition time by hours.

The following numbered paragraphs summarize significant features of various embodiments of this invention.

A medical device or prosthesis comprising a polymer body, wherein the polymer body comprises a plurality of polymer molecules located internally within said body, at least some of which internal polymer molecules have endgroups that comprise a surface of the body, wherein the surface endgroups include at least one surface-modifying amphipathic moiety, provided that at least some of said covalently bonded surface-modifying amphipathic moieties are other than alkylene ether-terminated poly(alkylene oxides).

The device or prosthesis of paragraph [0010], configured as an implantable medical device or prosthesis or as a non-implantable disposable or extracorporeal medical device or prosthesis or as an in vitro or an in vivo diagnostic device, wherein said device or prostheses has a tissue, fluid, and/or blood-contacting surface.

The device or prosthesis of paragraph [0010], wherein said polymer body comprises a dense or microporous membrane component in an implantable medical device or prosthesis or in a non-implantable disposable or extracorporeal medical device or prosthesis or as an in vitro or in vivo diagnostic device.

The device or prosthesis of paragraph [0012], wherein said polymer body comprises a membrane component in a diagnostic device and wherein said component contains immunoreactants.

The device or prosthesis of paragraph [0010], wherein said device or prosthesis comprises a blood gas sensor, a compositional sensor, a substrate for combinatorial chemistry, a customizable active biochip, a semiconductor-based device for identifying and determining the function of genes, genetic mutations, and proteins, a drug discovery device, an immunochemical detection device, a glucose sensor, a pH sensor, a blood pressure sensor, a vascular catheter, a cardiac assist device, a prosthetic heart valve, an artificial heart, a vascular stent, a prosthetic spinal disc, a prosthetic spinal nucleus, a spine fixation device, a prosthetic joint, a cartilage repair device, a prosthetic tendon, a prosthetic ligament, a drug delivery device from which drug molecules are released over time, a drug delivery coating in which drugs are fixed permanently to polymer endgroups, a catheter balloon, a glove, a wound dressing, a blood collection device, a blood storage container, a blood processing device, a plasma filter, a plasma filtration catheter, a device for bone or tissue fixation, a urinary stent, a urinary catheter, a contact lens, an intraocular lens, an ophthalmic drug delivery device, a male condom, a female condom, devices and collection equipment for treating human infertility, a pacemaker lead, an implantable defibrillator lead, a neural stimulation lead, a scaffold for cell growth or tissue engineering, a prosthetic or cosmetic breast implant, a prosthetic or cosmetic pectoral implant, a prosthetic or cosmetic gluteus implant, a penile implant, an incontinence device, a laparoscope, a vessel or organ occlusion device, a bone plug, a hybrid artificial organ containing transplanted tissue, an in vitro or in vivo cell culture device, a blood filter, blood tubing, roller pump tubing, a cardiotomy reservoir, an oxygenator membrane, a dialysis membrane, an artificial lung, an artificial liver, or a column packing adsorbent or chelation agent for purifying or separating blood, plasma, or other fluids.

A drug delivery device in accordance with paragraph [0014], wherein the drug is complexed to amphipathic surface-modifying endgroups and is released through diffusion.

A drug delivery device of paragraph [0014], wherein the drug is complexed or covalently bound to amphipathic surface-modifying endgroups that degrade and release the drug over time.

A packaging assembly comprising a polymer body, wherein the polymer body comprises a plurality of polymer molecules located internally within said body, at least some of which internal polymer molecules have endgroups that comprise a surface of the body, wherein the surface endgroups include at least one surface-modifying amphipathic moiety.

The packaging assembly of paragraph [0017], comprising a plastic bottle and eyedropper assembly containing a sterile solution, wherein said surface-modifying amphipathic moieties bind an antimicrobial agent and wherein said bound antimicrobial agents maintain the sterility of said solution.

An article comprising a polymer body, wherein the polymer body comprises a plurality of polymer molecules located internally within said body, at least some of which internal polymer molecules have endgroups that comprise a surface of the body, wherein the surface endgroups include at least one surface-modifying amphipathic moiety, provided that at least some of said covalently bonded surface-modifying amphipathic moieties are other than alkylene ether-terminated poly (alkylene oxides), and wherein the surface of the polymer body has enhanced aerodynamic or hydrodynamic drag, stealth properties, reduced or enhanced coefficient of friction, enhanced surface lubricity, enhanced ease of donning, enhanced wear properties, enhanced abrasive properties, enhanced or reduced static dissipation, enhanced or reduced energy absorption, or enhanced or reduced responsiveness to temperature, pH, electricity, or other stimuli.

The article of paragraph [0019], wherein the surface endgroups include a plurality of amphipathic endgroups each comprising a chain having multiple pendant hydrophobic groups along the chain, and the spacing between hydrophobic groups along the chains is such that interspersed hydrophilic segments assume low energy positions, and dendritic, columnar, tubular, or helical shapes are formed by self-assembly in the surface of the polymer body.

An article or device in which the nano surface architecture or micro surface architecture is a function of a variation in the chemical composition and molecular weight of amphipathic surface-modifying endgroups to enhance or reduce cell adhesion to biomedical implants or to tissue engineering scaffolds.

A method of configuring the nanostructure, supramolecular structure, and/or conformation of a molecular monolayer at a surface of a polymer body, which polymer body surface comprises a surface of an interface, which method comprises the step of contacting the polymer body surface with a medium that induces the delivery of amphipathic molecular moieties to the polymer body surface by interaction of chemical groups, chains, or oligomers, said amphipathic molecular moieties being covalently or ionically bonded to a polymer in the body and comprising one or more chemical groups, chains, or oligomers that spontaneously assemble in the outermost monolayer of the surface of the polymer body or one or more chemical groups, chains, or oligomers that spontaneously assemble within that portion of the polymer body that is at least one monolayer away form the outermost monolayer of the polymer body surface.

The method of paragraph [0022], wherein surface-modifying amphipathic moieties are delivered to the polymer body surface by their spontaneous diffusion to the surface region of the polymer body or by their rearrangement or repacking in the surface layer of the polymer body.

The method of paragraph [0022], wherein the polymer comprising the surface-modifying amphipathic moieties in the polymer body is a first polymer making up the entirety or a major portion of the body and having a weight average molecular weight in the range 5000-5,000,000 daltons (preferably 50,000-5,000,000 daltons), or is a second polymer, having a weight average molecular weight in the range 1000-500,000 daltons, which comprises an additive to the first polymer making up the entirety or a major portion of the body.

The method of paragraph [0024], in which the delivery of surface-modifying amphipathic moieties to the polymer body surface comprises adding a surface-active additive to the first polymer, said additive comprising a second polymer that is covalently or ionically bonded to said surface-modifying amphipathic moieties, wherein said surface-modifying amphipathic moieties may be endgroups of said second polymer.

The method of paragraph [0024], in which the delivery of surface-modifying amphipathic moieties to the polymer body surface comprises coating or otherwise topically treating the surface of the polymer body with a material comprising a second polymer covalently or ionically bonded to said surface-modifying amphipathic moieties, wherein said surface-modifying amphipathic moieties may be endgroups of said second polymer.

A method of configuring the nanostructure, supramolecular structure, and/or conformation of a molecular monolayer at a surface of a polymer body, which polymer body surface comprises a surface of an interface, which method comprises the sequential steps of contacting the polymer body surface with a medium that delivers amphipathic molecular moieties containing crosslinkable reactive groups to the polymer body surface by interaction of chemical groups, chains, or oligomers, said amphipathic molecular moieties being covalently or ionically bonded to a polymer in the body and comprising one or more chemical groups, chains, or oligomers that spontaneously assemble in the outermost monolayer of the surface of the polymer body or one or more chemical groups, chains, or oligomers that spontaneously assemble within that portion of the polymer body that is at least one monolayer away form the outermost monolayer of the polymer body surface, and crosslinking said crosslinkable reactive groups.

The method of paragraph [0027], wherein said amphipathic molecular moieties containing crosslinkable reactive groups comprise methoxy ether-terminated polyethyleneoxide oligomers having one or more acryloxy or methacryloxy groups along the polyethyleneoxide chain.

A method of immobilizing a protein or a peptide at a surface of a polymer body, which polymer body surface comprises a surface of an interface, which method comprises the sequential steps of contacting the polymer body surface with a medium that delivers amphipathic molecular moieties containing chemically-reactive groups, capable of binding biologically-active entities to the surface, to the polymer body surface by interaction of chemical groups, chains, or oligomers, said amphipathic molecular moieties being covalently or ionically bonded to a polymer in the body and comprising one or more chemical groups, chains, or oligomers that spontaneously assemble in the outermost monolayer of the surface of the polymer body or one or more chemical groups, chains, or oligomers that spontaneously assemble within that portion of the polymer body that is at least one monolayer away form the outermost monolayer of the polymer body surface, and binding said proteins or peptide to said reactive groups.

The method of paragraph [0029], wherein said amphipathic molecular moieties containing binding groups comprise methoxy ether-terminated polyethyleneoxide oligomers having one or more amino, hydroxyl, or carboxyl groups along the polyethyleneoxide chain.

A method of providing amphipathic surface-modifying endgroups that self-assemble into distinct and controllable size domains in their nano surface architecture or micro surface architecture, which method comprises the step of varying the chemical composition and molecular weight of the surface-modifying endgroup by adding specific moieties or functional groups along a surface-modifying endgroup chain that cause the surface-modifying endgroups in said chain to self-assemble into helices, arches, or other non-planar secondary structures.

A block copolymer molecule having a polyurethane hard block, a polyoxyalkylene soft block, and at least two surface-modifying amphipathic moieties, wherein at least one of said moieties is a surface active endgroup having a chain that bears multiple pendant groups of different polarity or composition than the main chain of the surface active endgroup.

A polymer molecule comprising a polyoxyalkylene chain having at least one surface-modifying amphipathic moiety, wherein said moiety is a surface active hydrophilic endgroup having a chain bearing multiple pendant hydrophobic groups.

A methoxy ether-terminated polyethyleneoxide polymer which has a plurality of acryloxy, methacryloxy, or other crosslinkable reactive groups along a polyethyleneoxide chain.

A methoxy ether-terminated polyethyleneoxide polymer which has a plurality of amino, hydroxyl, carboxyl, or other groups capable of binding biologically-active molecules along a polyethyleneoxide chain.

A segmented block copolymer comprising from about 5 to 45 weight-% of at least one hard segment, from about 95 to 55 weight-% of at least one soft segment, and from about 0.1 to 15 weight-% of at least one surface-modifying amphipathic moiety, with the proviso that said surface-modifying amphipathic moiety is not an alkylene ether-terminated poly(alkylene oxide).

The segmented block copolymer of paragraph [0036], wherein said hard segment is selected from the group consisting of 4,4'diphenylmethanediisocyanate and ethylenediamine; 4,4'diphenylmethanediisocyanate, ethylenediamine, and 1,3-cyclohexanediamine; 4,4'diphenylmethanediisocyanate, ethylenediamine, and 2,2'-bis(hydroxymethyl)propionic acid; a prepolymer of 4,4'diphenylmethanediisocyanate and butanediol; and 4,4'diphenylmethanediisocyanate, said soft segment is selected from the group consisting of polyalkyleneoxides (for instance: polytetramethylene oxide polylol or polyamine; polyhexamethylene oxide polyol or polyamine); polyalkylenecarbonates (for instance: polyhexamethylenecarbonate polyol or polyhexamethylenecarbonate polyamine; polyhexamethylenecarbonate-co-ethylenecarbonate polyol or polyhexamethylenecarbonate-co-ethylenecarbonate polyamine); polyethylenebutylenes; optionally-hydrogenated polybutadiene; optionally-hydrogenated polyisoprene; polyisobutylene polyols or polyamines; and blends of polytetramethylene oxide and polypropylene oxide-polyethylene oxide copolymer polyethers, and said surface-modifying amphipathic moiety is a methoxy ether-terminated polyethylene oxide having one or more acryl or methacryl groups or amino, hydroxyl, or carboxyl groups along the polyethyleneoxide chain.

A polymeric composition of matter having the formula

wherein B is a polymer block, C is a polymer block that may be the same as or different from B, and D is a polymer block that may be the same as one of or different from both of B and C, n is a number from 5 through $10^5$, A is a surface active endgroup, A' is a surface-modifying amphipathic moiety different from A, Z is a surface-modifying amphipathic moiety that may be the same as one of or different from both of A and A', and Z' is a surface active endgroup that is different from Z but may be the same as one of or different from both of A and A', with the proviso that at least one of A' and Z is other than an alkylene ether-terminated poly(alkylene oxide), and p and q may be the same or different and each is a number from 0 through 1.

The polymeric composition of matter of paragraph [0038], wherein A' and Z are methoxy ether-terminated polyethylene oxides having one or more crosslinkable reactive groups or groups capable of binding biologically-active molecules along the polyethyleneoxide chain.

The polymeric composition of matter of paragraph [0039], wherein said crosslinkable reactive groups are acryloxy and/or methacryloxy groups and wherein said groups capable of binding biologically-active molecules are amino, hydroxyl, and/or carboxyl groups.

The polymeric composition of matter of paragraph [0038], wherein D is the same as C, p is 0, q is 0, B is a polymeric block selected from the group consisting of polyurethanes, polyureas, polyamides, aromatic polyesters, aromatic polycarbonates, polystyrenes, and polyacrylates, C is a polymeric block selected from the group consisting of polyalkyleneoxides (for instance: polytetramethylene oxide polylol or polyamine; polyhexamethylene oxide polyol or polyamine); polyalkylenecarbonates (for instance: polyhexamethylenecarbonate polyol or polyhexamethylenecarbonate polyamine; polyhexamethylenecarbonate-co-ethylenecarbonate polyol or polyhexamethylenecarbonate-co-ethylenecarbonate polyamine); polyethylenebutylenes; optionally-hydrogenated polybutadiene; optionally-hydrogenated polyisoprene; polyisobutylene polyols or polyamines; and blends of polytetramethylene oxide and polypropylene oxide-polyethylene oxide copolymer polyethers, aliphatic polyesters (for instance, polycaprolactone), A is an endgroup selected from the group consisting of a polydimethylsiloxanes and poly(ethylene oxides), and Z is a methoxy ether-terminated polyethylene oxide which has one or more crosslinkable reactive groups or groups capable of binding biologically-active molecules along the polyethyleneoxide chain.

The polymeric composition of matter of paragraph [0038], wherein D is the same as C which in turn is the same as B.

The polymeric composition of matter of paragraph [0038], wherein D is the same as B and wherein C is different from B.

The polymeric composition of matter of paragraph [0038], wherein p and q are both 1 and wherein A, B, C, D, and Z are all different from one another.

A surface-modifying amphipathic moiety-containing polymer that comprises a linear base polymer having covalently bonded surface-modifying amphipathic moieties comprised of surface active endgroups of a nature and present in an amount such that said polymer has a contact angle hysteresis of the surface that is changed by at least 10% from the contact angle hysteresis of the surface of an otherwise identical polymer that does not contain said covalently bonded surface-modifying amphipathic moieties, provided that said covalently bonded surface-modifying amphipathic moieties are not alkylene ether-terminated poly(alkylene oxides).

DETAILED DESCRIPTION OF PREFERRED EMBODIMENTS

A "surface-modifying amphipathic moiety"-containing polymer molecule endgroup is defined as an endgroup that contains at least two moieties of significantly differing composition, such that the amphipathic endgroup spontaneously rearranges its positioning in a polymer body to position the moiety on the surface of the body depending upon the composition of the medium with which the body is in contact, which positioning effects a reduction in interfacial energy.

The amphipathic structure may comprise one or more chemical groups, chains, or oligomers that spontaneously assemble in the outermost monolayer of the surface of the polymer body, or may comprise one or more chemical groups, chains, or oligomers that spontaneously assemble within the bulk of the polymer body. The polymer bulk is defined as the region within the polymer body that is at least one monolayer away from the outermost monolayer of the polymer body surface. The location of said spontaneous assembly is governed by the interaction of the chemical groups, chains, or oligomers with a medium in contact with the polymer body surface. Said interaction may differ depending upon the temperature at which contact of the medium with the surface occurs.

An example of an "amphipathic" endgroup of a polymer molecule is an endgroup that contains at least two moieties of significantly differing polarities. The structure of the amphipathic endgroup is such that the amphipathic endgroup rearranges its positioning in a polymer body to position the more polar (hydrophilic) moiety or the more nonpolar (hydrophobic) moiety on the surface of the body, depending upon the polarity of a fluid with which the body is in contact.

Whether a particular polymer includes an amphipathic endgroup for purpose of the present invention can be determined by a simple analysis using SFG intensity spectra. One takes a first SFG intensity chart of the endgroup compound itself (independently of the polymer). Note that the functional group that potentially renders the endgroup amphipathic may constitute less than 10% of the mass of the endgroup compound. One takes a second SFG intensity chart of an endgroup compound derivative minus the functional group that potentially renders the endgroup amphipathic. One compares the two SFG intensity graphs. If a peak on the first SFG chart is attributable to the functional group that potentially renders the endgroup amphipathic, the polymer does in fact contain a surface-modifying amphipathic moiety. This technique can detect most functional groups quite readily. With respect to some groups which are known not to be strongly SFG active, such as $CF_3$ and $SO_3$, their presence in amphipathic endgroups can be established using this technique through careful comparison of spectra.

Figure 8:
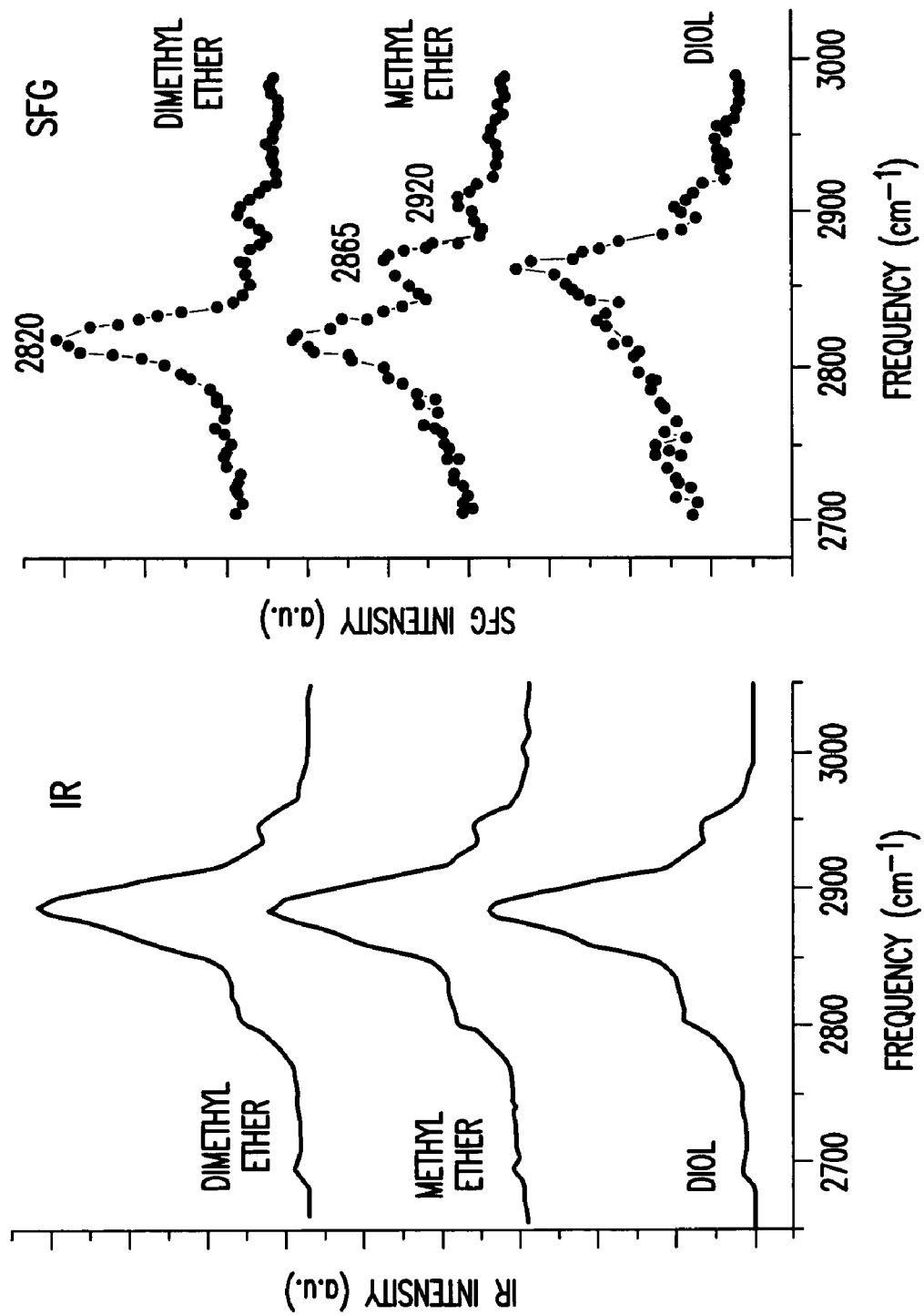
FIG. 8 shows comparative IR and SFG spectra for a polyethylene glycol and two derivatives thereof.

An example will elucidate this test. FIG. 8 relates to a polyethylene glycol having a molecular weight of approximately 2000 daltons. Three SFG intensity spectra are depicted in FIG. 8. The lowest spectrum is of the polyethylene glycol as such—that is, an α,ω-dihydroxypoly(ethylene oxide). It has no peak at 2820 $cm^{-1}$. The peak at 2865 $cm^{-1}$ is attributed to the —$CH_2O$— moieties that constitute a major portion of the mass of the polyethylene glycol. The middle spectrum is of polyethylene glycol monomethyl ether—that is, an α-methoxy-ω-hydroxypoly(ethylene oxide). It has a peak at 2820 $cm^{-1}$. The peak at 2820 $cm^{-1}$ is attributed to the $CH_3O$— moieties, even though such moieties make up only a very small part of the total mass of the polyethylene glycol monomethyl ether!

As will be clear from the SFG spectra presented hereinbelow, the presence of surface-modifying amphipathic moieties can also be detected by surface structure changes in "before" and "after" water (or other solvent) contact tests. Surface configuration changes due to SMAMs can also be detected by SFG spectra generated before and after cell adhesion or protein adsorption.

Also, U.S. Pat. No. 5,589,563 provides descriptions of useful SME chemistries that are defined by differences in various surface properties relative to the base polymer to which they would be attached, including contact angle, solid surface tension, and critical surface tension. In each case, useful differences between these values are given for a surface made up of SME-free base polymer and a homopolymer with a chemistry based on the SME only. The '563 patent is expressly incorporated by reference in this regard. Thus, for instance, if various moieties in a putative SMAM (in the form of homopolymers) differ in surface or interfacial tension by, for instance, at least 1 dyne/cm, or if they have contact angle hysteresis values that differ by at least 5%, then the SME would be an SMAM.

The Novel Methods

This invention provides a method of configuring the nanostructure, supramolecular structure, and/or conformation of a molecular monolayer at a surface of a polymer body at an interface. The method involves contacting the polymer body surface with a separate medium that induces the delivery of amphipathic molecular moieties to the polymer body surface. This delivery is due to the interaction of chemical groups, chains, or oligomers in the amphipathic moieties. The amphipathic molecular moieties are covalently or ionically bonded to a polymer in the body and include one or more chemical groups, chains, or oligomers that spontaneously assemble in the outermost monolayer of the surface of the polymer body or one or more chemical groups, chains, or oligomers that spontaneously assemble within that portion of the polymer body that is at least one monolayer away form the outermost monolayer of the polymer body surface.

In this method, the surface-modifying amphipathic moieties may be delivered to the polymer body surface by their spontaneous diffusion to the surface region of the polymer body or by their rearrangement or repacking in the surface layer of the polymer body.

Preferably, the polymer comprising the surface-modifying amphipathic moieties in the polymer body is a first polymer making up the entirety or a major portion of the body and having a weight average molecular weight in the range 5000-5,000,000 daltons (more preferably, in the range 50,000-5,000,000 daltons), or is a second polymer, having a weight average molecular weight in the range 1000-500,000 daltons (more preferably, in the range 5000-500,000 daltons, even more preferably in the range 15,000-500,000 daltons), which second polymer comprises an additive to the first polymer making up the entirety or a major portion of the body. Optionally, delivery of surface-modifying amphipathic moieties to the polymer body surface can be accomplished by adding a surface-active additive to the first polymer, with the additive comprising a second polymer that is covalently or ionically bonded to the surface-modifying amphipathic moieties. Such surface-modifying amphipathic moieties may be endgroups of said second polymer. Alternatively, delivery of surface-modifying amphipathic moieties to the polymer body surface may be accomplished by coating or otherwise topically treating the surface of the polymer body with a material comprising a second polymer covalently or ionically bonded to said surface-modifying amphipathic moieties, again wherein those surface-modifying amphipathic moieties may be endgroups of the second polymer.

This invention also provides method of configuring the nanostructure, supramolecular structure, and/or conformation of a molecular monolayer at a surface of a polymer body when the polymer body surface comprises a surface of an interface. This method includes the sequential steps of contacting the polymer body surface with a medium that delivers amphipathic molecular moieties (for instance, methoxy ether-terminated polyethyleneoxide oligomers) containing crosslinkable reactive groups (for instance, acryloxy or methacryloxy groups) to the polymer body surface by interaction of chemical groups, chains, or oligomers, and crosslinking said crosslinkable reactive groups. These amphipathic molecular moieties are covalently or ionically bonded to a polymer in the body and comprising one or more chemical groups, chains, or oligomers that spontaneously assemble in the outermost monolayer of the surface of the polymer body or one or more chemical groups, chains, or oligomers that spontaneously assemble within that portion of the polymer body that is at least one monolayer away form the outermost monolayer of the polymer body surface.

Another method of this invention is the method of immobilizing a protein or a peptide at an interfacial surface of a polymer body. This method comprises the sequential steps of (a) contacting the polymer body surface with a medium that delivers amphipathic molecular moieties (for instance, methoxy ether-terminated polyethylenexide oligomers) containing chemically-reactive groups, capable of binding biologically-active entities to the surface (for instance, one or more amino, hydroxyl, and/or carboxyl groups) to the polymer body surface by interaction of chemical groups, chains, or oligomers and (b) binding the proteins or peptides to the reactive groups. These amphipathic molecular moieties are covalently or ionically bonded to a polymer in the body and comprise one or more chemical groups, chains, or oligomers that spontaneously assemble in the outermost monolayer of the surface of the polymer body or one or more chemical groups, chains, or oligomers that spontaneously assemble within that portion of the polymer body that is at least one monolayer away form the outermost monolayer of the polymer body surface.

Yet another method of this invention is a method of providing amphipathic surface-modifying endgroups that self-assemble into distinct and controllable size domains in their nano surface architecture or micro surface architecture. This method varies the chemical composition and molecular weight of the surface-modifying endgroup by adding specific moieties or functional groups along a surface-modifying endgroup chain that cause the surface-modifying endgroups in the chain to self-assemble into helices, arches, or other non-planar secondary structures, as desired.

Sum Frequency Generation Analysis

The analysis required to investigate the domination of the chemical composition of a surface provided by surface-modifying endgroups that have been designed to migrate to an article's surface must probe only the outermost monolayer of the article in order to obtain an accurate representation of the surface composition. Historically, it has been a challenge to directly obtain such detailed information about surface structure due to the lack of molecular level techniques that specifically probe the molecules at a surface or interface. Various spectroscopic techniques—including reflection infrared spectroscopy, attenuated total reflection infrared spectroscopy, and Raman spectroscopy—have been used to characterize polymer surfaces. These methods, however, lack surface specificity and the resulting spectra are often obscured by the response from the bulk. Surface-sensitive techniques such as contact angle measurement, neutron reflection, and X-ray photoelectron spectroscopy often do not provide structural information, and/or do not allow for in situ measurement.

Recently, a surface-specific analytical technique with monolayer sensitivity has been developed. It has successfully been applied it to various kinds of surfaces and interfaces. Through IR and visible sum-frequency generation spectroscopy (SFG), a powerful and versatile in situ surface probe has been created that not only permits identification of surface molecular species, but also provides information about orientation of functional groups at the surface. SFG has the common advantages of laser techniques. That is, it is nondestructive, highly sensitive, and has good spatial, temporal, and spectral resolution.

During an SFG experiment, two laser beams are overlapped both in time and space on a polymer surface. The first laser is a fixed visible green beam with a wavelength of 532 nm ($\omega_{vis}$). The second laser is a tunable infrared beam ($\omega_{IR}$) in the wavelength range between 2 and 10 μm (1000-4000 cm$^{-1}$). The visible and IR beams mix on the surface to drive an oscillating dipole which then emits a coherent beam of photons at the sum of the visible and IR frequencies ($\omega_{SFG}=\omega_{vis}+\omega_{IR}$). A photo multiplier tube easily detects this generated beam to record a vibrational spectrum.

Under the electric dipole approximation, the intensity of the sum frequency signal is proportional to the square of the second-order nonlinear surface susceptibility ($I \propto |X^{(2)}|^2$). The susceptibility is described by the equation $$\chi^{(2)} = A_{NR} + \sum_R \frac{A_R}{(\omega_{IR} - \omega_0 - i\gamma)}$$

where $A_{NR}$ is the non-resonant contribution, $\gamma$ is the line width, $\omega_o$ is the resonant vibrational frequency, and $\omega_{IR}$ is the IR frequency. The resonant strength, $A_R$, is proportional to the concentration and orientation of molecules on the surface and the infrared and Raman transition moments. As observed in this equation, when $\omega_{IR}$ is equal to $\omega_o$, $X^{(2)}$ is maximized and so a surface vibrational spectrum can be obtained by scanning $\omega^{IR}$ through a frequency range of interest.

Since $A_R$ is proportional to the IR and Raman transition moments, the selection rules for both IR and Raman spectroscopy must be obeyed. Hence, a media must be both IR-active and Raman-active. From group theory, it can be shown that only media that lack inversion symmetry will satisfy this requirement. Usually, bulk materials are centrosymmetric and therefore do not generate SFG. Isotropic gasses and liquids also do not generate SFG. Only at surfaces or interfaces where the centrosymmetry of the bulk material is broken can SFG occur, therefore, SFG is extremely surface specific.

SFG is surface specific for many polymers because the bulk is amorphous; there is no net orientation of the polymer chains. Because of this random orientation, $X^{(2)}$ vanishes, and SFG is not allowed. A polymer surface however can have a net orientation of backbone atoms or functional groups at its surface, which leads to polar ordering. $X^{(2)}$ is then non-zero for a polymer surface, and is therefore SFG allowed. The orientation of molecules at the surface can also be determined by SFG. As described earlier, $X^{(2)}$ is proportional to the orientation of surface molecules. $X^{(2)}$ is a third rank tensor and the net orientation of surface molecules can be deduced by probing the surface with different polarizations of light. By changing the polarization of the input and output beams, different components of the tensor are accessed.

Because SFG is surface specific, the technique can be used to probe any interface as long as the media the laser beams must pass through do not interfere with the light. Examples of the interfaces accessible by SFG include but are not limited to the polymer/gas interface and the polymer/liquid interface The SFG apparatus is a complex laser system based on a high-power picosecond Nd:YAG laser and an optical parametric generator/amplifier (OPG/OPA). The fundamental output (1064 nm) of the Nd:YAG laser is frequency doubled to produce the 532 nm visible beam and is used to drive an OPO/OPA. The tunable (1000 to 4000 cm$^{-1}$) IR beam is generated from a series of non-linear crystals through OPG/OPA and difference frequency mixing. The sum-frequency (SF) spectra are obtained by overlapping the visible and IR beams on the polymer surface at incident angles of 55° and 60°, respectively. The SF signal from the polymer surface is filtered by a monochromator, collected by a photomultiplier tube (PMT), and processed using gated integrator. Surface vibrational spectra are obtained by measuring the SF signal as a function of the input IR frequency.

The films tested in Examples 1-7 below were films of PurSil 20 80A polymers or Elasthane 80A polymers. Elasthane 80A is a polyether urethane, having a Shore A hardness of about 80, made by reacting polytetramethylene oxide with 4,4'methylene bisphenyl diisocyanate chain-extended with 1,4-butanediol. PurSil 20 80A is a silicone-polyether-urethane, having a silicone content of 20 weight-% and a Shore A Hardness of about 80, made by reacting polydimethylsiloxane and polytetramethylene oxide with 4,4'methylene bisphenyl diisocyanate chain-extended with 1,4-butanediol. In both of these polymers, the copolymer chains are terminated with surface-modifying endgroups, as specified in each Example.

In the Examples that follow, SFG was acquired on polymer films with acquisition times of over 2 hours. Several peaks were observed for the various samples. On the materials that included amphipathic methoxy ether-terminated polyethylene oxide (MPEO) endgroups, a cloudy film was observed on the surface after long exposure to air. When this cloudy film was observed, a large additional peak at 2810 cm$^{-1}$ (assigned to the O—CH$_3$ stretching mode) was visible in the SFG spectra.

COMPARATIVE EXAMPLE 1

PurSil 20 80A

PurSil 20 80A has endgroups of the formula

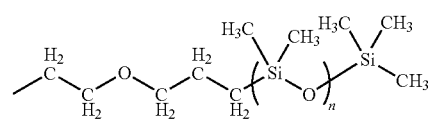

Figure 1:
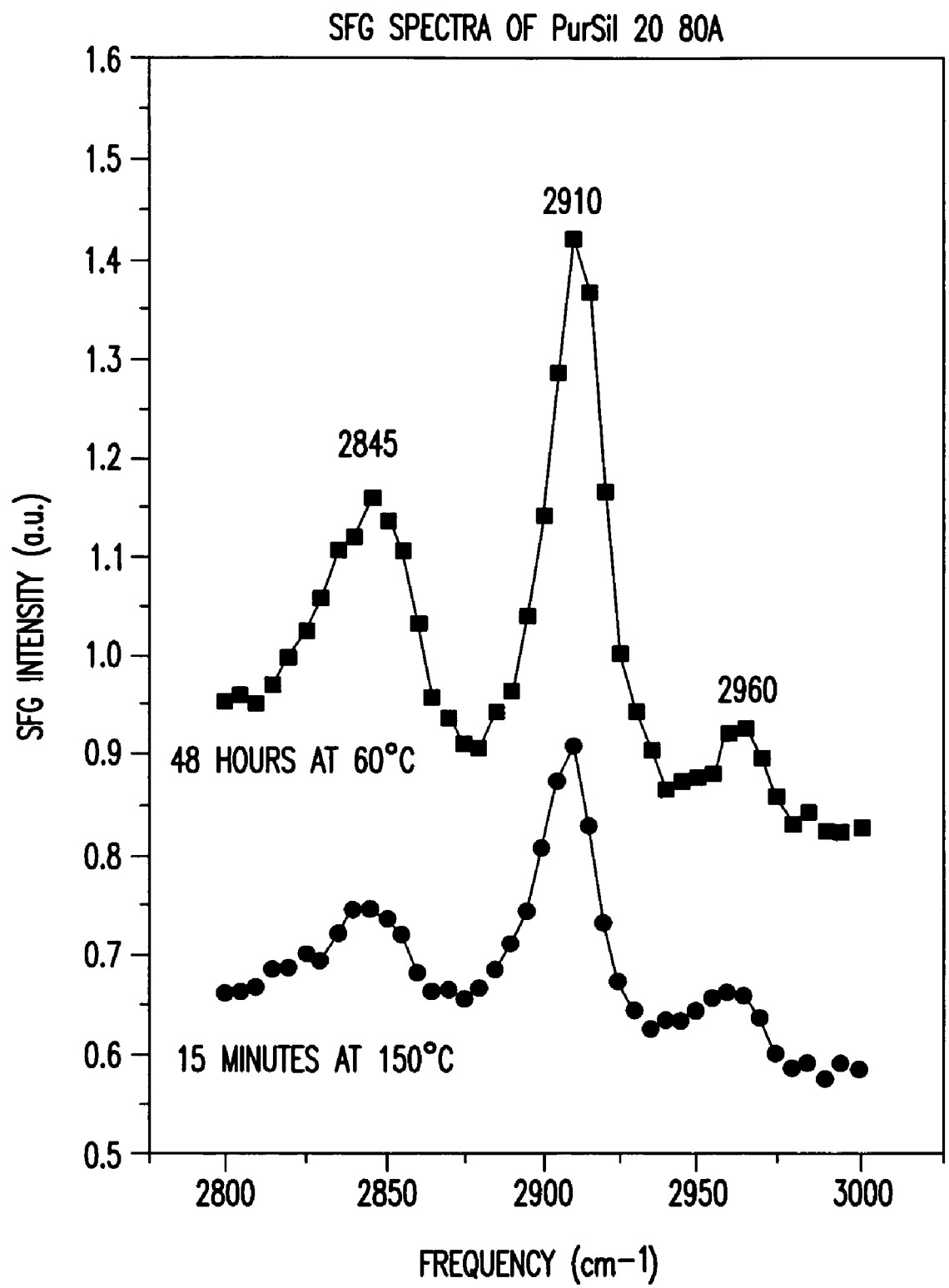
FIG. 1 depicts SFG spectra of PurSil 20 80A.

FIG. 1 shows the SFG spectra of PurSil 20 80A samples exposed for 48 hours at 60° C. and 15 minutes at 150° C. In both samples, the same three features were observed in similar relative proportion. The spectra were dominated by the symmetric stretch of Si—CH$_3$ groups. Additional peaks at 2845 and 2960 cm$^{-1}$ were observed and are attributed to the symmetric CH$_2$ stretch and a Fermi resonance, respectively. Essentially, no changes in the samples were observed.

EXAMPLE 2

Elasthane 80A with MPEO Amphipathic Endgroups

These Elasthane 80A polymers have endgroups of the formula

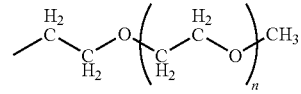

Figure 2:
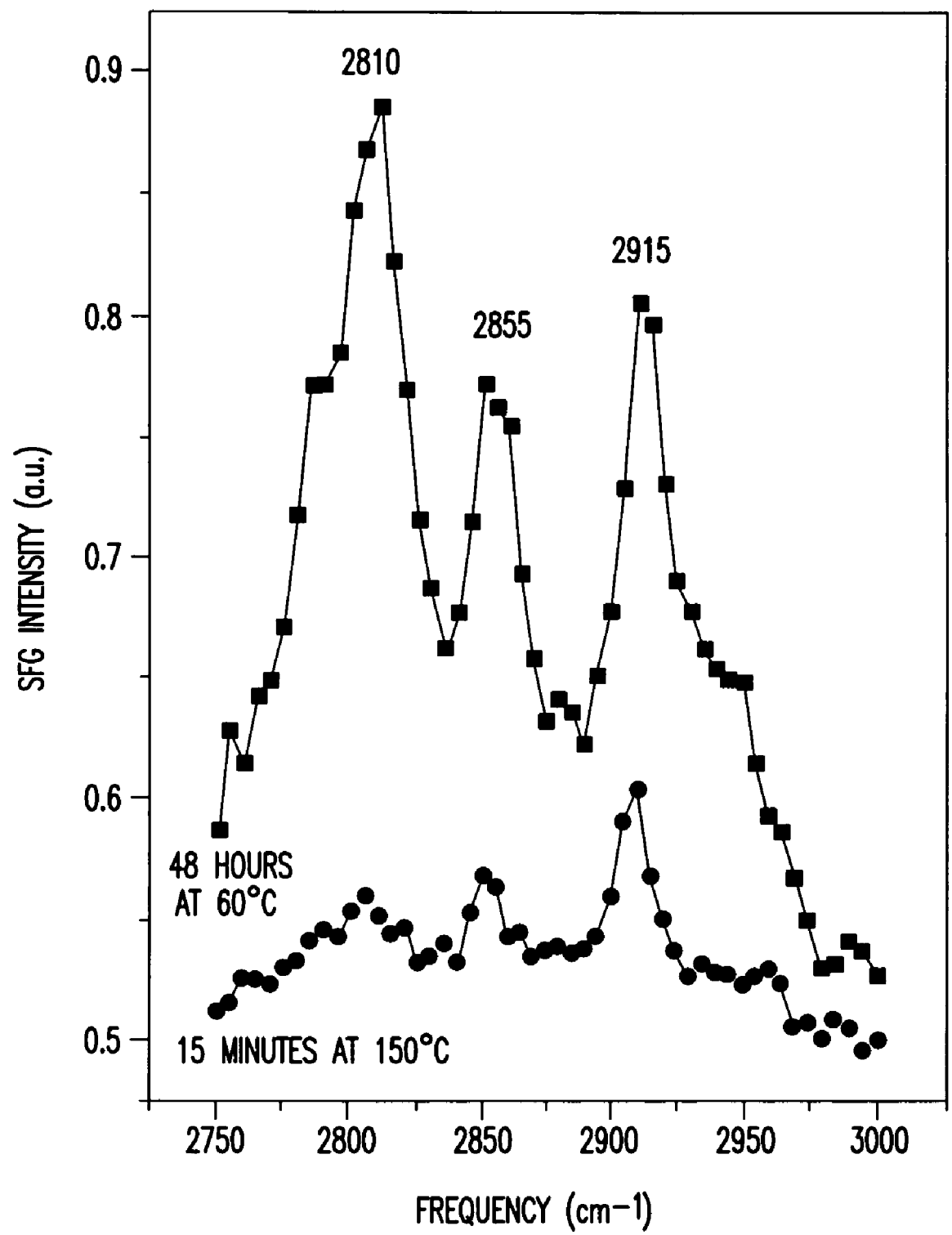
FIG. 2 depicts SFG spectra of Elasthane 80A with MPEO amphipathic endgroups.

FIG. 2 shows the SFG spectra of these Elasthane 80A samples, exposed for 48 hours at 60° C. and 15 minutes at 150° C. The sample treated at 60° C. was very opaque due to the cloudy film. A large peak was observed at 2810 cm$^{-1}$. The sample treated at 150° C. was slightly opaque, and the peak at 2810 cm$^{-1}$ was considerably smaller. This change in the peak ratios between spectra is due to a reorientation of surface species in the amphipathic endgroups, which results in a change in the surface concentration of one species (etheric oxygen) relative to another (CH$_2$).

COMPARATIVE EXAMPLE 3

Elasthane 80A Without Wax

Elasthane 80A without any added wax (a common processing aid) has endgroups of the formula

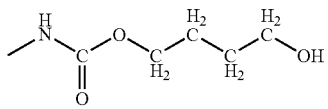

Figure 3:
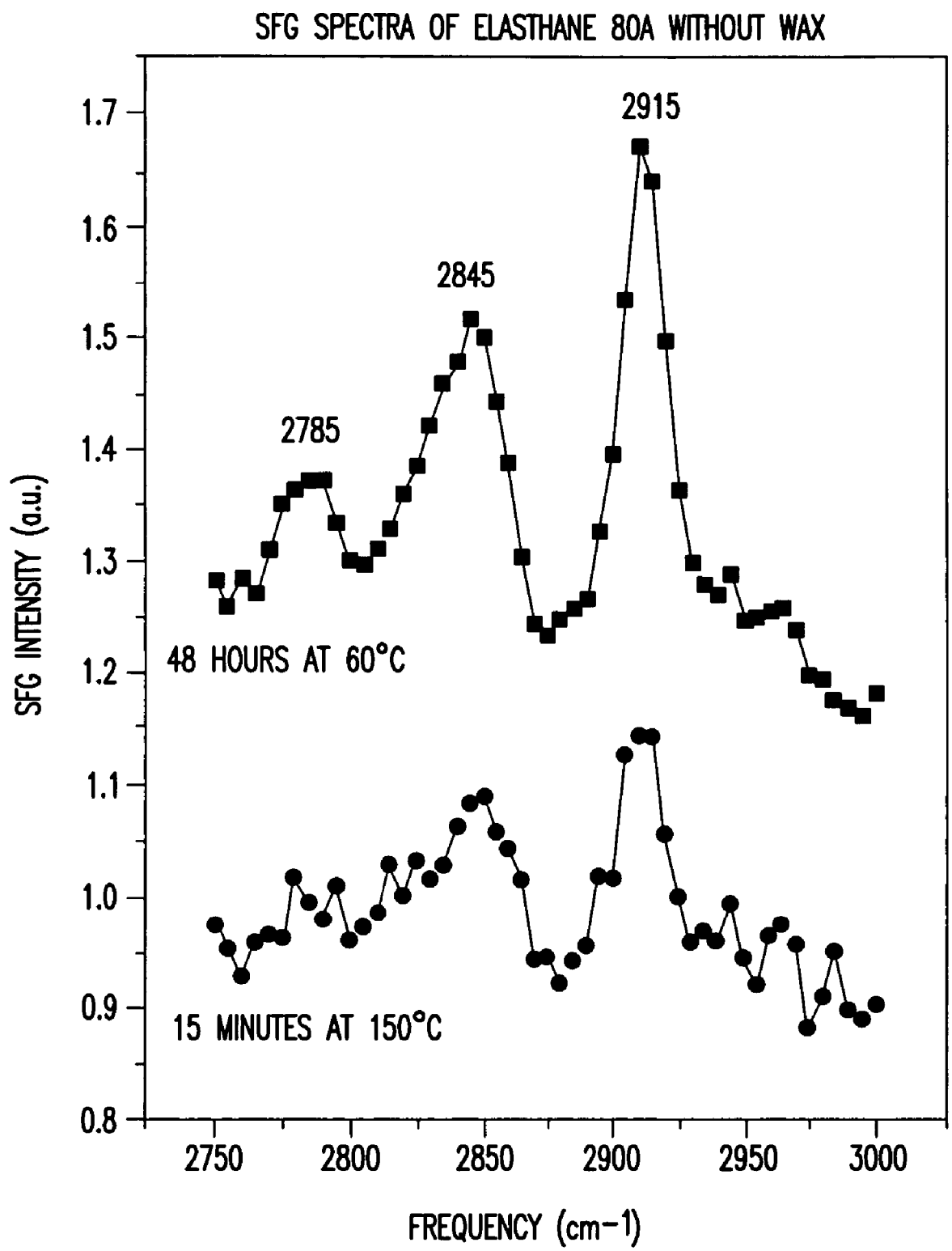
FIG. 3 depicts SFG spectra of Elasthane 80A without wax.

FIG. 3 shows the SFG spectra of samples of Elasthane 80A without wax, exposed for 48 hours at 60° C. and 15 minutes at 150° C. This polymer does not have amphipathic endgroups. A peak at 2785 cm$^{-1}$ was observed for the sample heated at 60° C. and is assigned to symmetric O—CH$_2$ groups next to urethane segments. Because the peak at 2785 cm$^{-1}$ decreased in relative intensity, it is likely that the O—CH$_2$ groups moved from the surface into the bulk upon heating to 150° C. Peaks at 2845 cm$^{-1}$ and 2910 cm$^{-1}$ were observed and assigned to the symmetric and asymmetric CH$_2$ stretches. The signal-to-noise ratio was much larger for the 60° C. sample as compared for the 150° C. sample because of the poor sample reflection quality.

EXAMPLE 4

PurSil 20 80A with MPEO Amphipathic Endgroups

These PurSil 20 80A polymers have endgroups of the formula

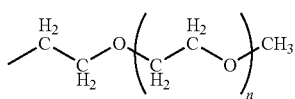

Figure 4:
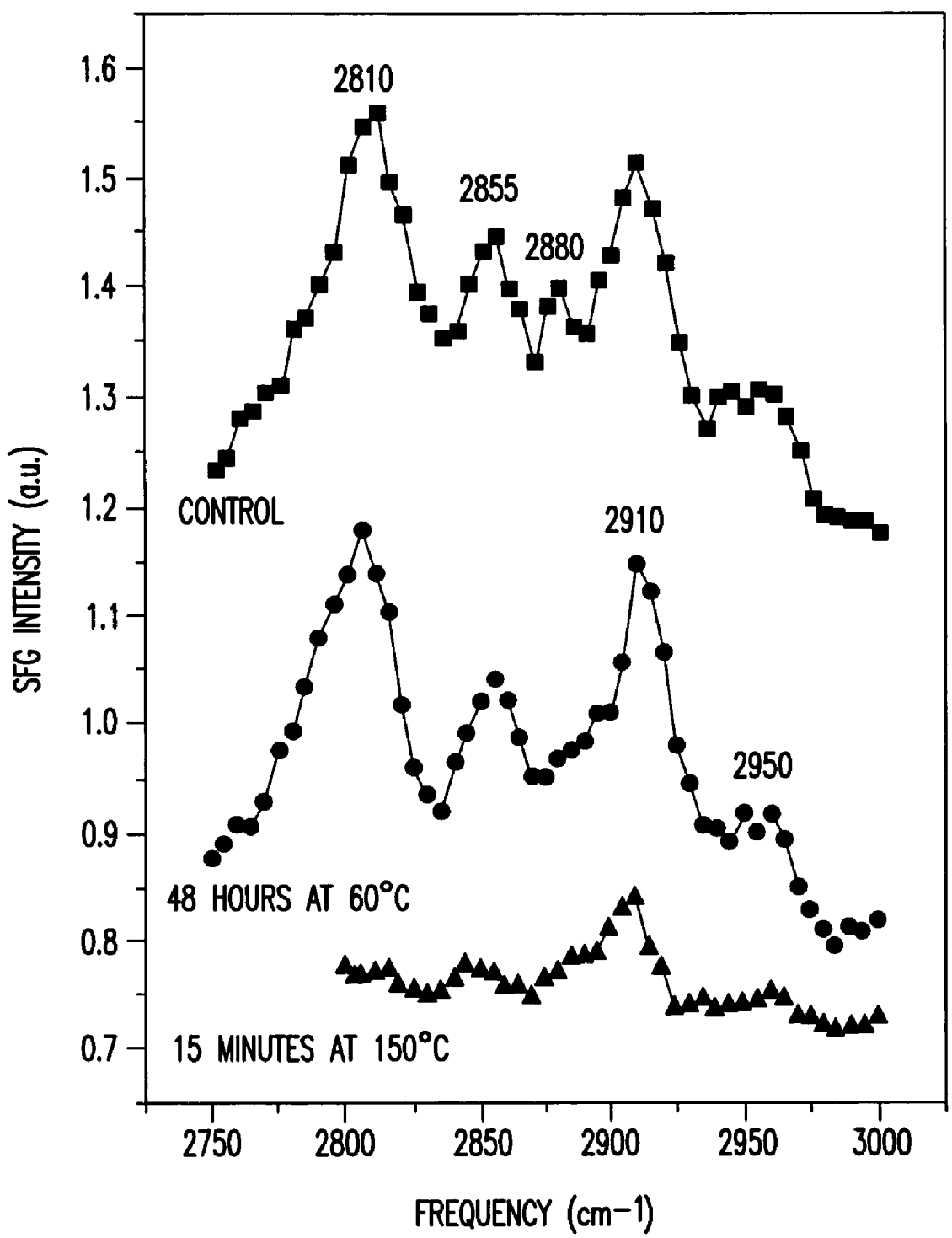
FIG. 4 depicts SFG spectra of PurSil 20 80A with MPEO amphipathic endgroups.

FIG. 4 shows the SFG spectra of three samples of PurSil 20 80A with MPEO amphipathic endgroups. One sample is a control, one sample was exposed for 48 hours at 60° C., and one sample was exposed for 15 minutes at 150° C. All three samples exhibited the cloudy film, and both the control and the sample treated at 60° C. revealed large peaks at 2810 cm$^{-1}$. The control sample also revealed a resolved peak at 2880 cm$^{-1}$, while the 60° C. sample and the 150° C. sample exhibited only shoulders at this frequency. The peak at 2880 cm$^{-1}$ is most likely due to the asymmetric stretch of the methyl groups that terminate the polymer chains. The symmetric O—CH$_2$ stretch peak is either hidden by the 2810 cm$^{-1}$ peak or the vibrational mode is parallel to the surface. The signal-to-noise ration of the 150° C. sample is smaller due to the poor reflection quality of the sample.

COMPARATIVE EXAMPLE 5

PurSil 20 80A SO$_3$

PurSil 20 80A SO$_3$ has endgroups of the formula

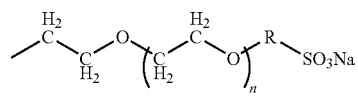

Figure 5:
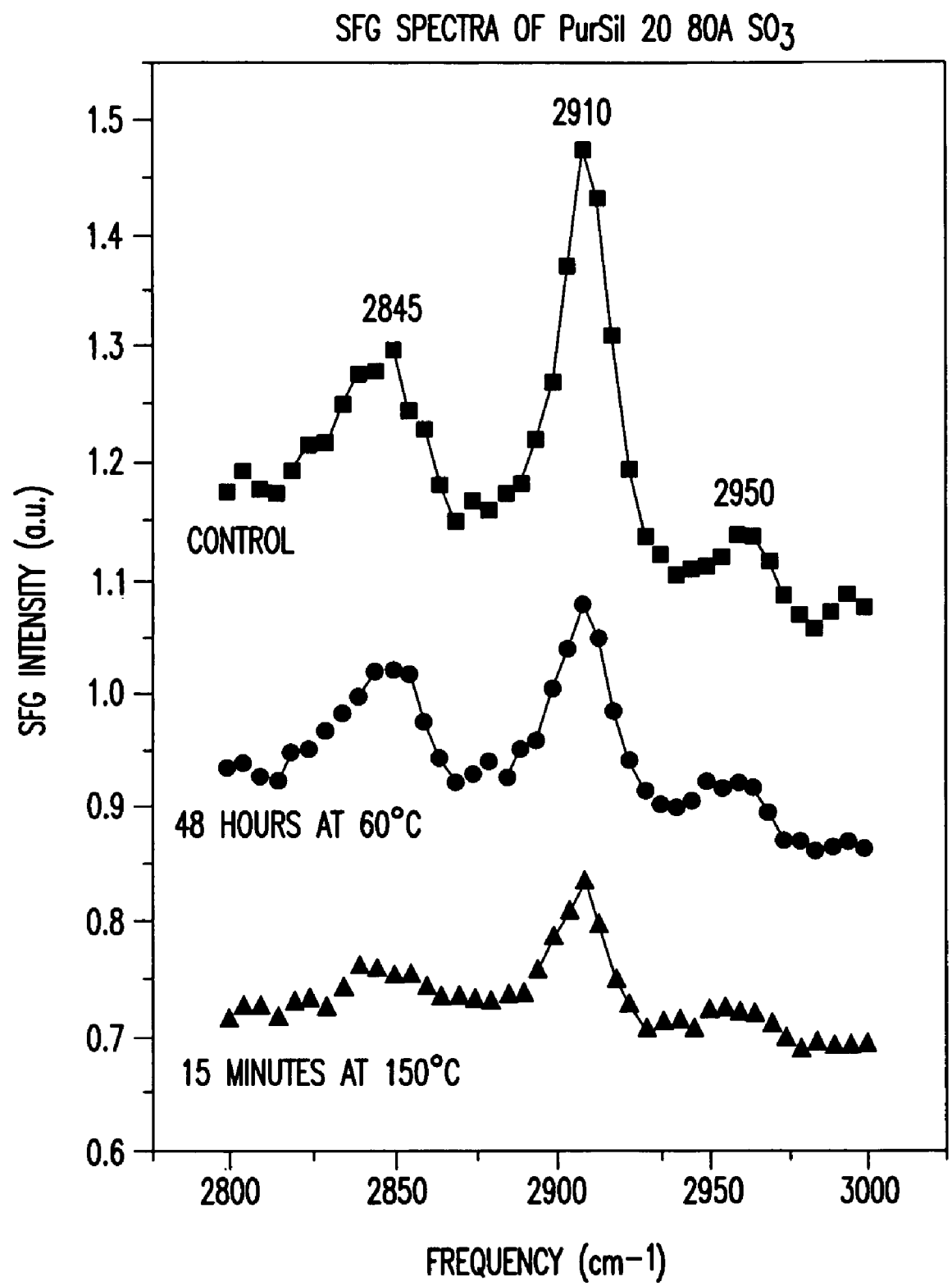
FIG. 5 depicts SFG spectra of PurSil 20 80A $SO_3$.

FIG. 5 shows the SFG spectra of PurSil 20 80A SO$_3$ samples exposed for 48 hours at 60° C. and 15 minutes at 150° C., along with a control sample. The qualitative features of the spectra are essentially identical, although the intensities are different due to different reflection qualities. The spectra are dominated by the Si—C$_{H3}$ peak at 2910 cm$^{-1}$. Additionally, the symmetric CH$_2$ stretch and Fermi resonance are observed at 2850 cm$^{-1}$ and 2950 cm$^{-1}$, respectively. There is no apparent change in the sample as it is heated to different temperatures.

EXAMPLE 6

PurSil 20 80A with MPEO Amphipathic Endgroups

These PurSil 20 80A polymers have endgroups of the formula

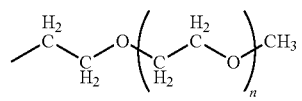

Figure 6:
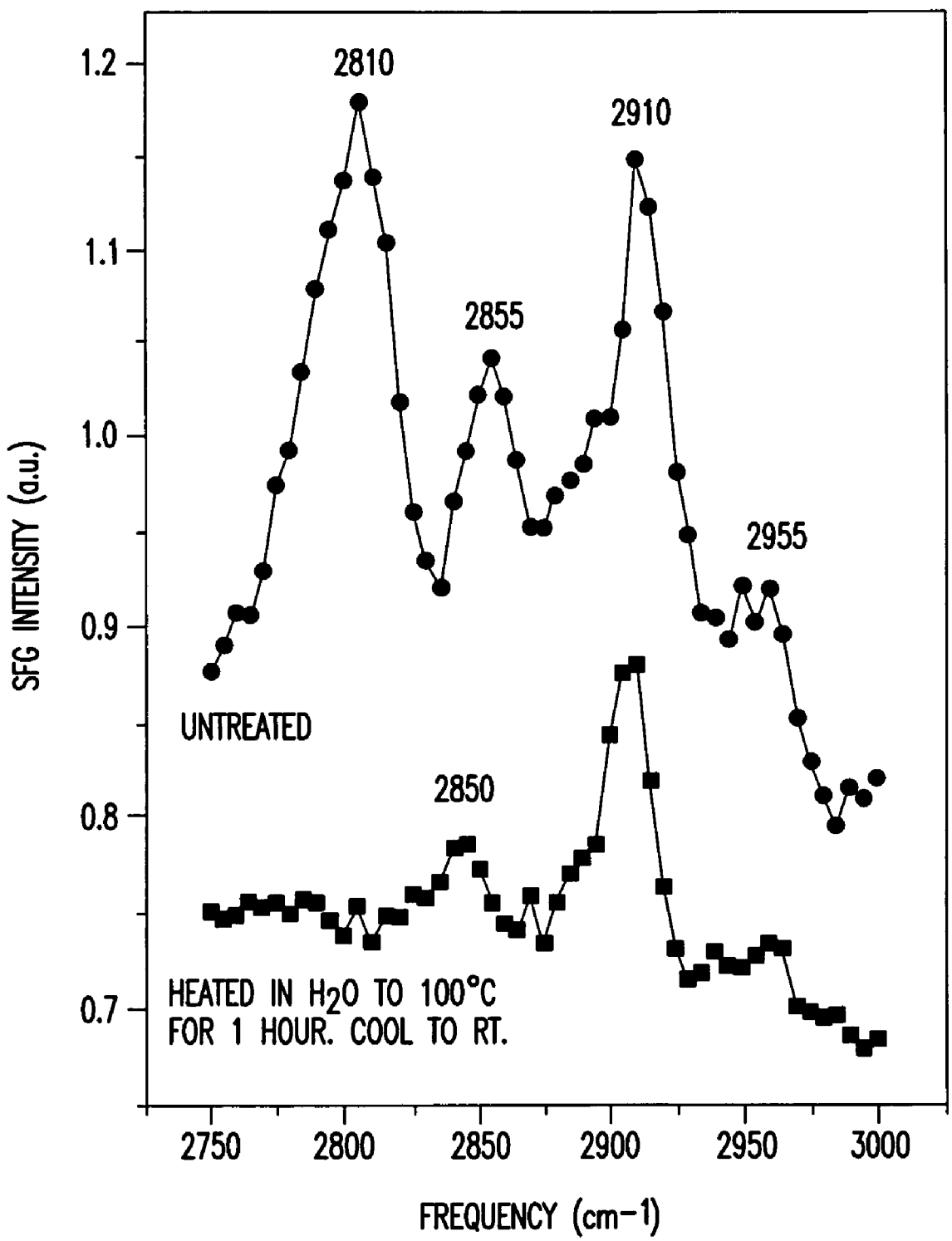
FIG. 6 depicts SFG spectra of PurSil 20 80A with MPEO amphipathic endgroups.

FIG. 6 shows the SFG spectra of two samples of PurSil 20 80A with MPEO amphipathic endgroups. One sample is a control, and one sample was heated in deionized water for 1 hour at 100° C. The large peak at 2810 cm$^{-1}$ is observed for the untreated sample. After heating in deionized water for 1 hour, the 2810$^{-1}$ peak is no longer observed. At this point, only features at 2845$^{-1}$, 2910$^{-1}$, and 2955$^{-1}$ are seen in the SFG spectrum. Also, the cloudy film was not observed for the sample heated in deionized water.

EXAMPLE 7

Elasthane 80A with MPEO Amphipathic Endgroups

These Elasthane 80A polymers have endgroups of the formula

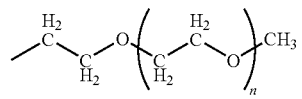

Figure 7:
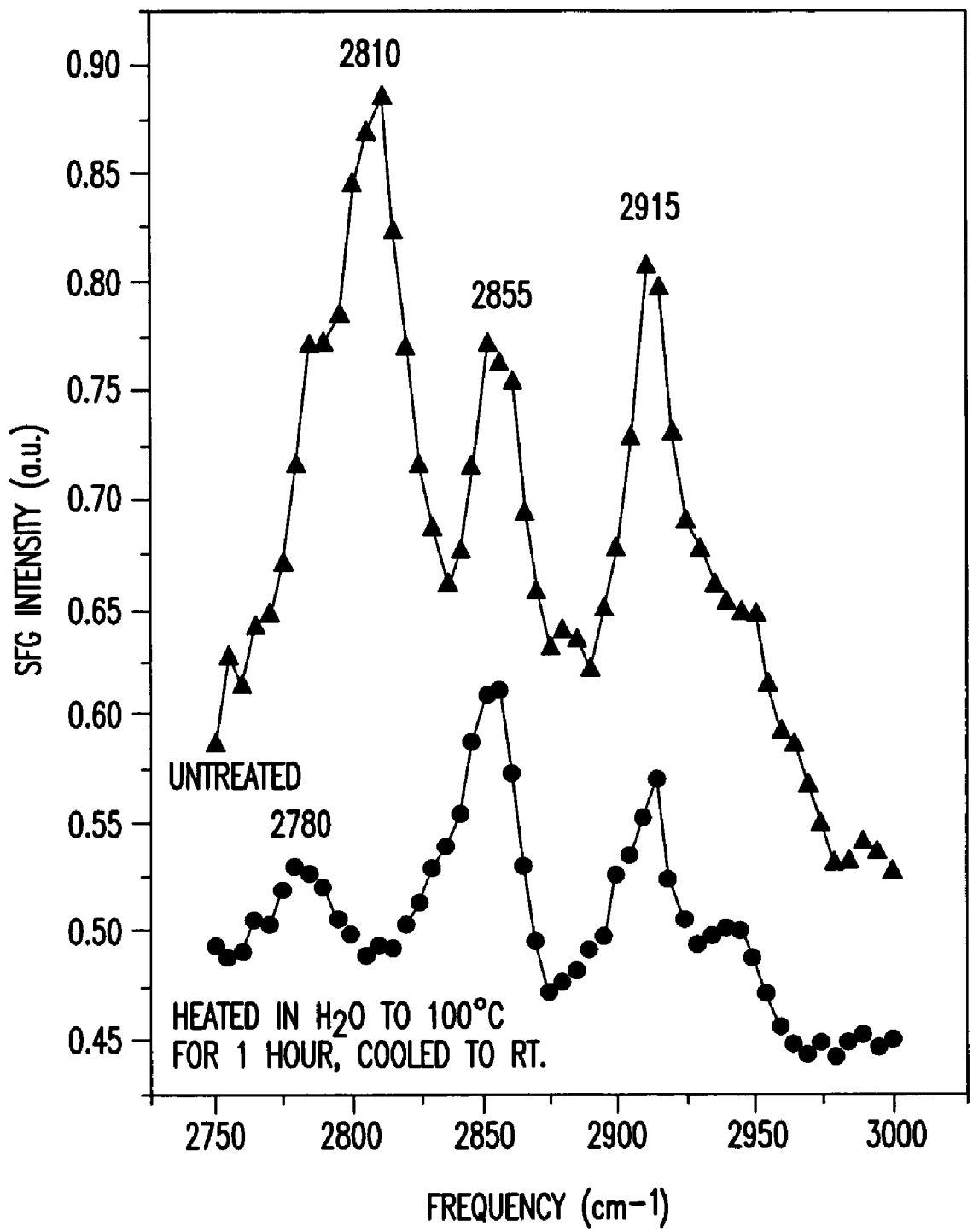
FIG. 7 depicts SFG spectra of Elasthane 80A with MPEO amphipathic endgroups.

FIG. 7 shows the SFG spectra of these Elasthane 80A samples. One sample is a control, and one sample was heated in deionized water for 1 hour at 100° C. Again, the cloudy film and the peak at 2810 cm$^{-1}$ were observed for the untreated sample. The SFG spectrum after heating in water does not show the peak at 2810 cm$^{-1}$ and the cloudy film was not observed with this sample. Also, a peak at 2780 cm$^{-1}$ was now visible, unlike with the untreated sample. In addition, the 2850 cm$^{-1}$ and 2910 cm$^{-1}$ peak ratios are considerably different for the two spectra. The symmetric CH$_2$ stretch becomes dominant in the water-treated sample, indicating that the surface groups have reoriented themselves.

CONCLUSION. Examples 1-7 demonstrate that polymer surfaces relax to minimize interfacial energy, with hydrophobic groups dominating in the surface of polymer samples in air and hydrophilic groups dominating the surface of polymer samples in water. In PurSil 20 80A (Comparative Example 1), the polydimethylsiloxane segments are the most hydrophobic groups and the SFG air spectra are dominated by the Si—CH$_3$ stretch at 2910 cm$^{-1}$. For Elasthane 80A without wax (Comparative Example 3), the polytetramethylene oxide segments are the most hydrophobic and dominate the SFG spectra. Annealing these samples in air to higher temperatures does not change the overall interfacial energy, and the same surface is observed for the different annealing conditions. For the Elasthane 80A with MPEO amphipathic endgroups (Examples 2 and 7) and the PurSil 20 80A with MPEO amphipathic endgroups (Examples 4 and 6), a different hydrophobic group—the terminal methoxy ether group—dominates the surface, as demonstrated by SFG. This indicates that the polyethylene oxide endgroups are at or near the surface and are mobile enough to permit their terminal methoxy ether groups to minimize the interfacial energy. When these polymer samples are exposed to air, the polyethylene oxide at the surface slowly crystallized over time. (The crystallized surface can easily be seen in optical microscope pictures and in AFM images.) The crystallized surface is responsible for the cloudy film observed on the samples with the amphipathic endgroups (Examples 2, 4, 6, and 7). Once a crystallized polyethylene oxide surface is exposed to water, the crystallinity is broken up by the bound water and the surface becomes amorphous and clear. In addition, the SFG peak at 2810 cm$^{-1}$ is no longer observed, indicating that the methoxy ether groups have moved below the surface.

Applications of the Novel Methods

Unconfigured SMAM-containing polymers may be converted to formed articles by conventional methods used to process polymers, including methods such as extrusion, injection molding, compression molding, calendering, and intensive mixing. SMAM polymers may also be processed by solution-based techniques, such as spraying, dipping, casting, and coating. Water-based SMAM polymer emulsions can be fabricated by methods similar to those used for solvent-based methods. In both cases, the evaporation of a volatile liquid (e.g., organic solvent or water) leaves behind a film of the SMAM polymer. These and other fabrication considerations which are applicable to the present invention are discussed in U.S. Pat. No. 5,589,563, the contents of which are hereby expressly incorporated by reference.

In general, surface-modifying amphipathic moieties have little or no negative effect on processability. In fact, certain SMAM-containing endgroups actually enhance processability of the polymers that incorporate them by favorably impacting wetting and spreading of the base polymer on mandrels or substrates to be coated. SMAM-containing polymers may also provide improved mold release properties, extrusion smoothness, polymer flow during compression molding, out-gassing and surface finish during solvent casting, coalescence of water-based emulsions, adhesion to substrates, and so on.

Polymers used to make useful articles in accordance with this invention will generally have tensile strengths of from about 350 to about 10,000 psi and elongations at break of from about 100 to about 1500%. In some particularly preferred embodiments, non-porous films of the present invention are provided in the form of flexible sheets or hollow membranes or fibers. Typically, such flexible sheets are prepared as long rollable sheets of about 10 to 15 inches in width and 1 to hundreds of feet in length. The thicknesses of these sheets may range from about 5 to about 100 microns. Thicknesses of from about 19 to 25 microns are particularly useful when the article to be manufactured is to be used without support or reinforcement.

When membranes are fabricated from the polymers of this invention by knife-over-roll casting onto release paper, web, or liner, for instance, a 24-foot-long 15-inch-wide continuous web coater equipped with forced-air ovens may be utilized. The coater may be modified for clean operation by fitting the air inlet ducts with High Efficiency Particulate Air filters. A nitrogen-purged coater box may be used to hold and dispense filtered polymer solutions or reactive prepolymer liquids. All but trace amounts of casting solvent (e.g., dimethylformamide) may be removed by the coater's hot air ovens fitted with HEPA filters. After membrane casting, the membrane and substrate may be further dried to reduce residual solvent content to less than about 100 ppm.

Polymer membranes of this invention may have any shape resulting from a process utilizing a liquid which is subsequently converted to a solid during or after fabrication, e.g., solutions, dispersion, 100% solids prepolymer liquids, polymer melts, etc. Converted shapes may also be further modified using methods such as die cutting, heat sealing, solvent or adhesive bonding, or any of a variety of other conventional fabrication methods.

In the case of essentially linear surface-modifying amphipathic moiety-containing polymers of this invention, thermoplastic fabrication methods may also be employed. Membrane polymers made by bulk or solvent-free polymerization method may be cast into, e.g., a Teflon-lined pan during the polymerization reaction. As the reaction proceeds and the polymerizing liquid becomes a rubbery solid, the pan may be post-cured in an oven, e.g. at 100-120° C. for about an hour. Upon cooling, the solid mass may be chopped into granules and dried in a dehumidifying hopper dryer for, e.g., about 16 hours. The dry granules may then be compression molded, e.g., at about 175° C., to form a flat membrane which, when cool, will have a thickness of about 50 mm. Extrusion, injection molding, calendering, and other conversion methods that are well-known in the art may also be employed to form membranes, films, and coatings of the polymers of the present invention configured into solid fibers, tubing, medical devices, and prostheses. As those skilled in the art will appreciate, these conversion methods may also be used for manufacturing components for non-medical product applications.

This invention thus provides medical devices or prostheses which are constituted of polymer bodies, wherein the polymer bodies comprise a plurality of polymer molecules located internally within said body, at least some of which internal polymer molecules have endgroups that comprise a surface of the body. The polymer bodies can include dense or microporous membrane components in implantable medical devices or prostheses or in non-implantable disposable or extracorporeal medical devices or prostheses. For example, in one embodiment, the polymer body may comprises a membrane component or coating containing immuno-reactants in a diagnostic device. The present invention is particularly adapted to provide such articles configured as implantable medical devices or prostheses or as non-implantable disposable or extracorporeal medical devices or prostheses or as in in vitro or in vivo diagnostic devices, wherein the device or prostheses has a tissue, fluid, and/or blood-contacting surface. Where the article of the present invention is a drug delivery device, the drug may be complexed to the SMAM endgroups and released through diffusion, or it may be complexed or covalently bound to SMAM endgroups which slowly degrade and release the drug over time. In accordance with this invention, the surface endgroups of the polymers include surface-modifying amphipathic moieties, provided that at least some of said covalently bonded surface-modifying amphipathic moieties are other than alkylene ether-terminated poly(alkylene oxides). These latter medical devices or prostheses are excluded from the present invention to the extent that they are disclosed in U.S. Pat. No. 5,589,563.

Those skilled in the art will thus appreciate that the present invention provides improved blood gas sensors, compositional sensors, substrates for combinatorial chemistry, customizable active biochips—that is, semiconductor-based devices for use in identifying and determining the function of genes, genetic mutations, and proteins, in applications including DNA synthesis/diagnostics, drug discovery, and immunochemical detection, glucose sensors, pH sensors, blood pressure sensors, vascular catheters, cardiac assist devices, prosthetic heart valves, artificial hearts, vascular stents and stent coatings, e.g., for use in the coronary arteries, the aorta, the vena cava, and the peripheral vascular circulation, prosthetic spinal discs, prosthetic spinal nuclei, spine fixation devices, prosthetic joints, cartilage repair devices, prosthetic tendons, prosthetic ligaments, drug delivery devices from which drug molecules are released over time, drug delivery coatings in which drugs are fixed permanently to polymer endgroups, catheter balloons, gloves, wound dressings, blood collection devices, blood processing devices, plasma filters, plasma filtration catheters and membranes, devices for bone or tissue fixation, urinary stents, urinary catheters, contact lenses, intraocular lenses, ophthalmic drug delivery devices, male and female condoms, devices and collection equipment for treating human infertility, insulation tubing and other components of pacemaker leads, implantable defibrillator leads, neural stimulation leads, scaffolds for cell growth or tissue engineering, prosthetic or cosmetic breast or pectoral or gluteal or penile implants, incontinence devices, devices for treating acid reflux disease, laparoscopes, vessel or organ occlusion devices, bone plugs, hybrid artificial organs containing transplanted tissue, in vitro or in vivo cell culture devices, blood filters, blood tubing, roller pump tubing, cardiotomy reservoirs, oxygenator membranes, dialysis membranes, artificial lungs, artificial livers, or column packing adsorbents or chelation agents for purifying or separating blood, plasma, or other fluids. All such articles can be made by conventional means, with the benefits of this invention being provided by the surface-modifying amphipathic endgroups that characterize the polymers described herein.

A variation of the above is plastic packaging for storing and/or dispensing sterile products. One example would be plastic bottle and eyedropper assemblies, which generally contain antimicrobial additives in addition to eye medication. In accordance with this invention, a polymer containing SMAMs that bind an antimicrobial such as benzalkonium chloride are incorporated into the packaging plastic, thus avoiding or reducing the need for such antimicrobial agents to be present in solution form within the packaging.

Those skilled in the art are also well aware of how to use such embodiments of the present invention. See for instance: Ebert, Stokes, McVenes, Ward, and Anderson, *Biostable Polyurethane Silicone Copolymers for Pacemaker Lead Insulation*, The 28$^{th}$ Annual Meeting of the Society for Biomaterials, Apr. 24-27, 2002, Tampa, Fla.; Ebert, Stokes, McVenes, Ward, and Anderson, *Polyurethane Lead Insulation Improvements using Surface Modifying Endgroups*, The 28$^{th}$ Annual Meeting of the Society for Biomaterials, Apr. 24-27, 2002, Tampa, Fla.; Litwak, Ward, Robinson, Yilgor, and Spatz, *Development of a Small Diameter, Compliant, Vascular Prosthesis*, Proceedings of the UCLA Symposium on Molecular and Cell Biology, Workshop on Tissue Engineering, February, 1988, Lake Tahoe, Calif.; Ward, White, Wolcott, Wang, Kuhn, Taylor, and John, "Development of a Hybrid Artificial Pancreas with Dense Polyurethane Membrane", *ASAIO Journal*, J. B. Lippincott, Vol. 39, No. 3, July-September 1993; Ward, White, Wang, and Wolcott, *A Hybrid Artificial Pancreas with a Dense Polyurethane Membrane: Materials & Design*, Proceedings of the 40$^{th}$ Anniversary Meeting of the American Society for Artificial Internal Organs, Apr. 14-16, 1994, San Francisco, Calif.; Farrar, Litwak, Lawson, Ward, White, Robinson, Rodvien, and Hill, "In-Vivo Evaluation of a New Thromboresistant Polyurethane for Artificial Heart Blood Pumps", *J. of Thoracic Surgery*, 95:191-200, 1987; and Jones, Soranno, Collier, Anderson, Ebert, Stokes, and Ward, *Effects of Polyurethanes with SMEs on Fibroblast Adhesion and Proliferation and Monocyte and Macrophage Adhesion*, The 28$^{th}$ Annual Meeting of the Society for Biomaterials, Apr. 24-27, 2002, Tampa, Fla., all of which references are hereby expressly incorporated by reference.

ANTICOAGULANT UTILITY EXAMPLES

Segmented polyurethane block copolymers having a poly (ethylene glycol) 1,4-bis{β-[N-methyl-N-(2-hydroxyethyl) amino]propionyl}piperazine (PEOPIME) or poly(ethylene glycol)-1-methyl-4-{β-[N-methyl-N-(2-hydroxyethyl) amino]propionyl}piperazine (PEOPDAMA) or poly(ethyleneglycol)phosphoryl choline (PEOPhC) surface-modifying amphipathic moiety is synthesized in accordance with Synthetic Examples 7, 8, and 9, below. Following that polymerization, a configured article is prepared from the polymer. The configured article, decorated with surface active groups, is exposed to a dilute heparin solution to bind heparin to the PEOPIME or the PEOPDAMA or the PEOPhC moiety. Heparin is a well-known anticoagulant in the prevention of thrombosis and thromboemboli. Polymers made in accordance with these Examples are particularly useful for making implantable, extracorporeal, or disposable medical devices and prostheses and diagnostic devices where blood contact occurs in use, such as catheters, catheter balloons, membranes, filters, blood collection devices and containers, roller pump tubing, cardiac assist devices, vascular grafts, etc.

Another embodiment of this invention is an article comprising a polymer body, wherein the polymer body comprises a plurality of polymer molecules located internally within the body, at least some of which internal polymer molecules have endgroups that comprise a surface of the body. In this embodiment, the surface endgroups include at least one surface-modifying amphipathic moiety, provided that at least some of said covalently bonded surface-modifying amphipathic moieties are other than alkylene ether-terminated poly(alkylene oxides). In accordance with this embodiment, the surface of the polymer body has enhanced antimicrobial properties, enhanced aerodynamic or hydrodynamic drag, stealth properties, reduced or enhanced coefficient of friction, enhanced surface lubricity, enhanced ease of donning, enhanced wear properties, enhanced abrasive properties, enhanced or reduced static dissipation, enhanced or reduced energy absorption, or enhanced or reduced responsiveness to temperature, pH, electricity, or other stimuli. In a preferred aspect of this embodiment of the invention, the surface endgroups include a plurality of amphipathic endgroups each comprising a chain having multiple pendant hydrophobic groups along the chain, and the spacing between hydrophobic groups along the chains is such that interspersed hydrophilic segments assume low energy positions. In this embodiment, dendritic, columnar, tubular, or helical shapes are formed by self-assembly in the surface of the polymer body.

Yet another embodiment of this invention provides an article or device in which the nano surface architecture or micro surface architecture is a function of a variation in the chemical composition and molecular weight of amphipathic surface-modifying endgroups to enhance or reduce cell adhesion to biomedical implants or to tissue engineering scaffolds.

New Compounds

As indicated in the BACKGROUND section above, U.S. Pat. No. 5,589,563 specifically describes two polymers that contain surface-modifying amphipathic moieties that can be used in the practice of aspects of the present invention described above. However, the present invention also contemplates polymeric compounds that are not specifically described in the '563 patent.

This invention provides a block copolymer molecule having a polyurethane hard block, a polyoxyalkylene soft block, and at least two surface-modifying amphipathic moieties (SMAMs), wherein at least one of the SMAM moieties is a surface active endgroup having a chain that bears multiple pendant groups of different polarity or composition than the main chain of the surface active endgroup.

This invention also provides a polymer molecule which incorporates a polyoxyalkylene chain having at least one surface-modifying amphipathic moiety, wherein said moiety is a surface active hydrophilic endgroup having a chain bearing multiple pendant hydrophobic groups. This embodiment of the invention includes methoxy ether-terminated polyethyleneoxide polymers having a plurality of acryloxy, methacryloxy, or other crosslinkable reactive groups along a polyethyleneoxide chain, as well as methoxy ether-terminated polyethyleneoxide polymers having a plurality of amino, hydroxyl, carboxyl, or other groups capable of binding biologically-active molecules along a polyethyleneoxide chain.

Another embodiment of this invention is a segmented block copolymer comprising from about 5 to 45 weight-% of at least one hard segment, from about 95 to 55 weight-% of at least one soft segment, and from about 0.1 to 15 weight-% of at least one surface-modifying amphipathic moiety, with the proviso that said surface-modifying amphipathic moiety is not an alkylene ether-terminated poly(alkylene oxide). The hard segment may be selected from the group consisting of 4,4'diphenylmethanediisocyanate and ethylenediamine; 4,4'diphenylmethanediisocyanate, ethylenediamine, and 1,3-cyclohexanediamine; 4,4'diphenylmethanediisocyanate, ethylenediamine, and 2,2'-bis(hydroxymethyl)propionic acid; a prepolymer of 4,4'diphenylmethanediisocyanate and butanediol; and 4,4'diphenylmethanediisocyanate. The soft segment may be selected from the group consisting of polytetramethylene oxide; polycarbonate polyol; polyisobutylene; optionally-hydrogenated polybutadiene polyol; and a blend of polytetramethylene oxide and polypropylene oxide-polyethylene oxide copolymer. The surface-modifying amphipathic moiety may be a methoxy ether-terminated polyethylene oxide having one or more acryl or methacryl groups or amino, hydroxyl, carboxyl, or phosphoryl choline groups along the polyethyleneoxide chain or at the terminal position of the polyethyleneoxide chain.

A further embodiment of the present invention is polymeric compositions of matter of the formula

$A_p A'_{1-p}[BCD]_n Z_q Z'_{1-q}$ wherein B is a polymer block, C is a polymer block that may be the same as or different from B, and D is a polymer block that may be the same as one of or different from both of B and C, n is a number from 5 through $10^5$, A is a surface active endgroup, A' is a surface-modifying amphipathic moiety different from A, Z is a surface-modifying amphipathic moiety that may be the same as one of or different from both of A and A', and Z' is a surface active endgroup that is different from Z but may be the same as one of or different from both of A and A', with the proviso that at least one of A' and Z is other than an alkylene ether-terminated poly(alkylene oxide), and p and q may be the same or different and each is a number from 0 through 1. One preferred sub-embodiment of this aspect of the invention includes the polymeric compositions of matter wherein A' and Z are methoxy ether-terminated polyethylene oxides having one or more crosslinkable reactive groups (e.g., acryloxy and/or methacryloxy groups) or groups capable of binding biologically-active molecules (e.g., amino, hydroxyl, and/or carboxyl groups) along the polyethyleneoxide chain. Another preferred sub-embodiment of this aspect of the invention includes polymeric compositions of matter wherein D is the same as C, p is 0, q is 0, B is a polymeric block selected from the group consisting of polyurethanes, polyureas, polyamides, aromatic polyesters, aromatic polycarbonates, polystyrenes, and polyacrylates, C is a polymeric block selected from the group consisting of polyethers, aliphatic polyesters, polyisoprenes, optionally-hydrogenated polyisoprenes, polyisobutylenes, optionally-hydrogenated polybutadienes, polyethylenebutylenes, and aliphatic polycarbonates, A is an endgroup selected from the group consisting of a polydimethylsiloxanes and poly(ethylene oxides), and Z is a methoxy ether-terminated polyethylene oxide which has one or more crosslinkable reactive groups or groups capable of binding biologically-active molecules along the polyethyleneoxide chain. Other preferred sub-embodiments of this aspect of the invention include the polymeric compositions of matter: wherein D is the same as C which in turn is the same as B; wherein D is the same as B and wherein C is different from B; and wherein p and q are both 1 and wherein A, B, C, D, and Z are all different from one another.

Yet another embodiment of the invention is a surface-modifying amphipathic moiety-containing polymer that comprises a linear base polymer having covalently bonded surface-modifying amphipathic moieties comprised of surface active endgroups of a nature and present in an amount such that said polymer has a contact angle hysteresis of the surface that is changed by at least 10% from the contact angle hysteresis of the surface of an otherwise identical polymer that does not contain said covalently bonded surface-modifying amphipathic moieties, provided that said covalently bonded surface-modifying amphipathic moieties are not alkylene ether-terminated poly(alkylene oxides).

Further disclosure relating to suitable polymer components and endgroup design is found in U.S. Pat. No. 5,589,563, the entire disclosure of which patent is hereby expressly incorporated by reference.

Synthesis: General Considerations

Exemplary synthetic methods are presented hereinbelow, based upon polyurethane chemistry, to teach how to make the polymers of this invention. Those skilled in the art will readily understand, however, based upon this disclosure, how to append surface-modifying amphipathic moieties (SMAMs) to other segmented and block copolymers, random copolymers, graft copolymers, and homopolymers. The polymers of this invention may be prepared as solution-based polymers (dissolved in organic solvent), as bulk polymers (100% solids, no solvent), as water-borne emulsions or dispersions (polymer dispersed in a water phase), or as one or multi-component castable polymers. Synthetic procedures, which would enable the preparation of a multitude of polymers by changing soft segments, isocyanates, chain extenders, and/or endgroups, are described below. More details relating to the synthetic methods that may be employed to make the SMAM-containing polymers of this invention may be found in U.S.

Pat. No. 5,589,563, the disclosure of which is hereby expressly incorporated by reference.

SYNTHETIC EXAMPLE 1

Solution-Based Synthesis

In this Example, the soft segment is a polytetramethylene oxide (PTMO) having a molecular weight of 2000, the hard segment is composed of 4,4'-diphenylmethane diisocyanate (MDI) having a molecular weight of 250.26 and ethylene diamine (ED) having a molecular weight of 60.1, and the endgroups are poly(ethylene glycol) acrylate (PEOAc) endgroups having a molecular weight of 375. A reactor is charged with 0.85 moles of polytetramethylene oxide and 0.07 moles of monofunctional OH-terminated poly(ethylene glycol) acrylate. The reactants are dried under vacuum with a nitrogen purge. Then 0.85 moles of 4,4'-diphenylmethane diisocyanate solution in dimethylacetamide is added to the reactor, and the contents of the reactor are further diluted with additional dimethylacetamide solvent. The ingredients are stirred for 3 hours at 55° C. The contents of the reactor are then diluted with more dimethylacetamide solvent, and cooled to 40° C. Polymer synthesis is completed by adding 0.77 moles of ethylene diamine in dimethylacetamide solvent and stirring at 40° C. for 30 minutes.

The resulting polymer has the following characteristics:

| Reactant | Molecular Weight | Weight-% | Moles |
| --- | --- | --- | --- |
| PTMO | 2000 | 77.26 | 0.85 |
| MDI | 250.26 | 19.44 | 1.7 |
| ED | 60.1 | 2.12 | 0.77 |
| PEOAc | 375 | 1.18 | 0.07 |

SYNTHETIC EXAMPLE 2

Water-Borne Synthesis

In this Example, 0.71 moles of polytetramethylene oxide (PTMO) are melted, dried under vacuum, and added to a reactor. Then 0.05 moles of monofunctional OH-terminated poly(ethylene glycol) methacrylate (PEOMa), 4.43 moles of dicyclohexylmethane 4,4"-diisocyanate (HMDI), 0.23 moles of 2,2"-bis(hydroxy methyl) propionic acid (DMPA) and a small amount of stannous octoate are added to the reactor. The ingredients are stirred for 45 minutes at 100° C., and subsequently the reactor contents are cooled to 65° C. This prepolymer is dispersed in triethylamine (TEA) water solution and stirred for 10 minutes. Then a solution of 3.38 moles of ethylene diamine (ED) are added, and stirring is continued for one hour. The solution is removed from the reactor and filter through an ASTM No. 50 sieve.

The resulting polymer has the following characteristics:

| Reactant | Molecular Weight | Weight-% | Moles |
| --- | --- | --- | --- |
| PTMO | 1000 | 33.2 | 0.71 |
| HMDI | 262 | 51.5 | 4.43 |
| DMPA | 134.13 | 1.39 | 0.23 |
| TEA | 101.19 | 1.05 | 0.1 |
| ED | 60.1 | 9.0 | 3.38 |
| PEOMa | 600 | 1.33 | 0.05 |

SYNTHETIC EXAMPLE 3

Bulk (Thermoplastic) Synthesis

In this Example, 0.85 moles of polytetramethylene oxide (PTMO) and 0.07 moles of monofunctional OH-terminated poly(ethylene glycol) monolaurate (PEOLau) are charged into a reactor and dried under vacuum with a nitrogen purge. Then 1.7 moles of 4,4'-diphenylmethane diisocyanate (MDI) are added and the ingredients are stirred for 30 minutes at 110° C. The polymer synthesis is completed by adding 0.77 moles of ethylene diamine (ED) and stirring for one minute.

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOLau | 600 | 1.18 | 0.07 |

SYNTHETIC EXAMPLE 4

Two-Component Castable Prepolymer Synthesis

In this Example, 1.7 moles of 4,4'-diphenylmethane diisocyanate (MDI) are charged into a reactor at 60° C. Then 0.85 moles of polytetramethylene oxide (PTMO) and 0.007 moles of monofunctional OH-terminated poly(ethylene glycol) methyl ether-block-polycaprolactone (PEOTone) are slowly added, keeping the exotherm between 60° C. and 90° C. This reaction is conducted for three hours, resulting in a prepolymer partially terminated with poly(ethylene glycol) methyl ether-block-polycaprolactone and containing an excess of isocyanate moieties. The prepolymer is subsequently cast with 0.77 moles of ethylene diamine (ED).

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOTone | 5000 | 1.18 | 0.007 |

SYNTHETIC EXAMPLE 5

A segmented polyurethane block copolymer is prepared by reacting a soft segment precursor polyol—polytetramethylene oxide—and a reactant containing a surface-modifying amphipathic moiety—monofunctional OH-terminated poly(ethylene glycol) lysine—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOLysine | 5000 | 1.18 | 0.007 |

SYNTHETIC EXAMPLE 6

A segmented polyurethane block copolymer is prepared by reacting a soft segment precursor polyol—polytetramethylene oxide—and a reactant containing a surface-modifying amphipathic moiety—monofunctional OH-terminated poly(ethylene glycol) arginine-glycine-aspartic acid-serine (PEOFNF)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOFNF | 5000 | 1.18 | 0.007 |

The formula for the surface-modifying amphipathic moiety PEOFNF is as follows:

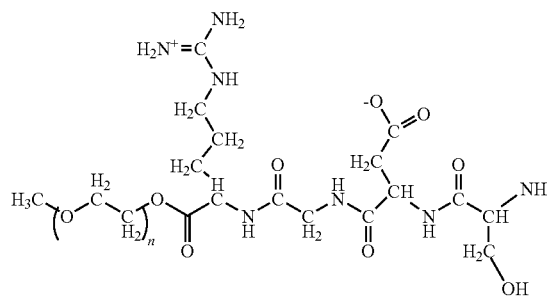

SYNTHETIC EXAMPLE 7

A segmented polyurethane block copolymer is prepared by reacting a soft segment precursor polyol—polytetramethylene oxide—and a reactant containing a surface-modifying amphipathic moiety—monofunctional OH-terminated poly(ethylene glycol)-1,4-bis {β-[N-methyl-N-(2-hydroxyethyl)amino]propionyl}piperazine (PEOPIME)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOPIME | 5000 | 1.18 | 0.007 |

The formula for the surface-modifying amphipathic moiety PEOPIME is as follows:

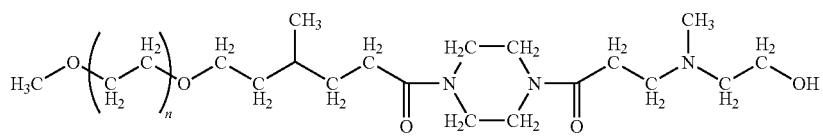

SYNTHETIC EXAMPLE 8

A segmented polyurethane block copolymer is prepared by reacting a soft segment precursor polyol—polytetramethylene oxide—and a reactant containing a surface-modifying amphipathic moiety—monofunctional OH-terminated poly(ethylene glycol)-1-methyl-4{β-[N-methyl-N-(2-hydroxyethyl)amino]propionyl}piperazine (PEOPDAMA)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOPDAMA | 5000 | 1.18 | 0.007 |

The formula for the surface-modifying amphipathic moiety PEOPDAMA is as follows:

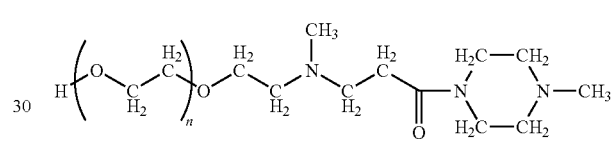

SYNTHETIC EXAMPLE 9

A segmented polyurethane block copolymer is prepared by reacting a soft segment precursor polyol—polytetramethylene oxide—and a reactant containing a surface-modifying amphipathic moiety—monofunctional OH-terminated poly(ethylene glycol)-zwitterionic phosphoryl choline (PEOPhC)— with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
| --- | --- | --- | --- |
| PTMO | 2000 | 76.72 | 0.85 |
| MDI | 250.26 | 19.3 | 1.7 |
| ED | 60.1 | 2.1 | 0.77 |
| PEOPhC | 5000 | 1.18 | 0.007 |

Formulae for the surface-modifying amphipathic moiety PEOPhC are as follows:

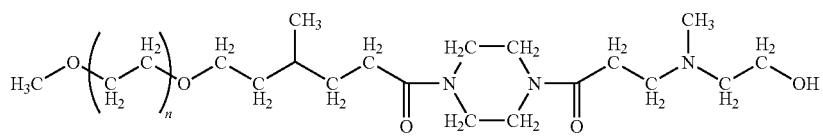

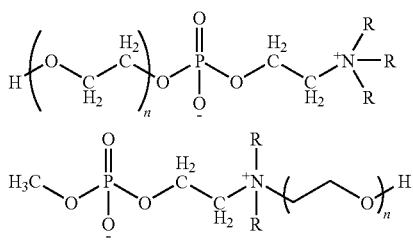

SYNTHETIC EXAMPLE 10

A segmented polyurethane block copolymer is prepared by reacting a soft segment precursor polyol—polytetramethylene oxide—and a reactant containing a surface-modifying amphipathic moiety—monofunctional NH$_2$-terminated poly(ethylene glycol) fibronectin fragment (PEOFNFr)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
|---|---|---|---|
| PTMO | 2000 | 76.72 | 0.85 |
| MDI | 250.26 | 19.3 | 1.7 |
| ED | 60.1 | 2.1 | 0.77 |
| PEOFNFr | 5000 | 1.18 | 0.007 |

SYNTHETIC EXAMPLE 11

A segmented polyurethane block copolymer is prepared by reacting a soft segment precursor polyol—specifically, polytetramethylene oxide—and a reactant containing a surface-modifying amphipathic moiety—specifically, monofunctional OH-terminated polyvinylpyrrolidone arginine-glycine-aspartic acid-serine (PVPFNF)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
|---|---|---|---|
| PTMO | 2000 | 76.72 | 0.85 |
| MDI | 250.26 | 19.3 | 1.7 |
| ED | 60.1 | 2.1 | 0.77 |
| PVPFNF | 5000 | 1.18 | 0.007 |

SYNTHETIC EXAMPLE 12

A segmented polyurethane block copolymer is prepared by reacting a soft segment precursor polyol—polytetramethylene oxide—and a reactant containing a surface-modifying amphipathic moiety—monofunctional OH-terminated poly(vinyl sulfonic acid) arginine-glycine-aspartic acid-serine (PSOFNF)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
|---|---|---|---|
| PTMO | 2000 | 76.72 | 0.85 |
| MDI | 250.26 | 19.3 | 1.7 |
| ED | 60.1 | 2.1 | 0.77 |
| PSOFNF | 5000 | 1.18 | 0.007 |

SYNTHETIC EXAMPLE 13

A segmented polyurethane block copolymer is prepared by reacting a soft segment precursor polyol—polytetramethylene oxide—and a reactant containing a surface-modifying amphipathic moiety—monofunctional OH-terminated poly(dimethylsiloxane) arginine-glycine-aspartic acid-serine (PDMSFNF)—with hard segment polyisocyanate precursors—4,4'-diphenylmethane diisocyanate and ethylene diamine—according to one of the synthetic procedures described in Examples 1-4.

The resulting polymer has the following characteristics:

| Reactant | Molecular Weight | Weight-% | Moles |
|---|---|---|---|
| PTMO | 2000 | 76.72 | 0.85 |
| MDI | 250.26 | 19.3 | 1.7 |
| ED | 60.1 | 2.1 | 0.77 |
| PDMSFNF | 5000 | 1.18 | 0.007 |

The formula for the surface-modifying amphipathic moiety PDMSFNF is as follows:

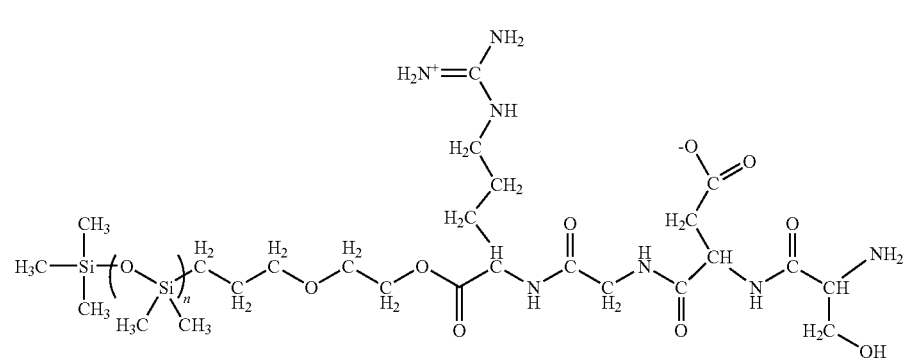

SYNTHETIC EXAMPLE 14 ('563 patent Ex. 8)

A segmented polyurethane block copolymer is prepared by reacting a soft segment precursor—polyisobutylene (PIB)—and a reactant containing a surface-modifying amphipathic moiety—a monofunctional $NH_2$-terminated methoxy ether-terminated poly(ethylene oxide) (MPEO)— with hard segment polyisocyanate precursors—4,4'-diphenylmethane diisocyanate, ethylene diamine (ED), and 1,3-cyclohexanediamine (CHD)—according to one of the synthetic procedures described in Examples 1-4.

The resulting polymer has the following characteristics:

| Reactant | Molecular Weight | Weight-% | Moles |
|---|---|---|---|
| PIB | 2000 | 71.18 | 6.69 |
| MDI | 250.26 | 16.27 | 12.22 |
| ED | 60.1 | 1.30 | 4.05 |
| CHD | 114.19 | 0.60 | 1 |
| MPEO | 2000 | 10.65 | 1 |

SYNTHETIC EXAMPLE 15 ('563 patent Ex. 6)

A segmented polyurethane block copolymer is prepared by reacting a soft segment precursor—polyethylene oxide (PEO) and polyethylene oxide-polypropylene oxide copolymer (PPO-PEO)—and a reactant containing a surface-modifying amphipathic moiety—a monofunctional $NH_2$-terminated methoxy ether-terminated poly(ethylene oxide) (MPEO)—and a surface-modifying endgroup—a monofunctional OH-terminated polydimethylsiloxane (MPSX)—with hard segment polyisocyanate precursors—4,4'-diphenylmethane diisocyanate and ethylene diamine (ED)—according to one of the synthetic procedures described in Examples 1-4.

The resulting polymer has the following characteristics:

| Reactant | Molecular Weight | Weight-% | Moles |
|---|---|---|---|
| PPO-PEO | 1972 | 7.98 | 2 |
| PEO | 1475 | 53.0 | 7.98 |
| MDI | 250.26 | 19.94 | 18.98 |
| ED | 60.1 | 2.16 | 7.98 |
| MPSX | 2000 | 8.94 | 1 |
| MPEO | 2000 | 7.98 | 1 |

The present invention has been illustrated by reference to certain specific embodiments thereof. However, those skilled in the art will readily appreciate that other, different embodiments can be practiced using the principles of the invention. All said embodiments constitute a part of the invention patented to the extent that they are reflected in the appended claims.

What is claimed is:

1. An implantable medical device or prosthesis or a non-implantable disposable or extracorporeal medical device or prosthesis or an in vitro or in vivo diagnostic device, wherein said device or prosthesis has a tissue, fluid, and/or blood-contacting surface, comprising a polymer body, wherein the polymer body comprises a plurality of polymer molecules located internally within said body, at least some of which internal polymer molecules have endgroups that comprise a surface of the body, wherein the surface endgroups include at least one surface-modifying amphipathic moiety, wherein the polymer comprising the surface-modifying amphipathic moieties in the polymer body is a polymeric composition of matter having the formula $$A[BC]_nZ$$

wherein B is a polymeric block selected from the group consisting of polyurethanes, polyureas, polyamides, aromatic polyesters, aromatic polycarbonates, polystyrenes, and polyacrylates, C is a polymeric block selected from the group consisting of polyethers, aliphatic polyesters, polyisoprenes, optionally-hydrogenated polyisoprenes, polyisobutylenes, optionally-hydrogenated polybutadienes, polyethylenebutylenes, and aliphatic polycarbonates, n is a number from 5 through $10^5$, A is a surface active endgroup selected from the group consisting of polydimethylsiloxane chains and poly(ethylene oxide) chains having one or more amino-, hydroxyl-, carboxyl-, phosphoryl choline-, acryloxy-, or methacryloxy-containing moieties along the chain or at the terminal position thereof, and Z is a surface active endgroup that may be the same as or different from A, wherein said polymeric composition of matter has a weight average molecular weight in the range 5000-5,000,000 daltons.

2. The device or prosthesis of claim 1, wherein Z is the same as A and said one or more amino-containing moieties are polyvinylpyrrolidone groups.

3. The device or prosthesis of claim 1, wherein said polymeric composition of matter has a weight average molecular weight in the range 50,000-5,000,000 daltons.

4. The device or prosthesis of claim 1, wherein said polymer body comprises a dense or microporous membrane component in an implantable medical device or prosthesis or in a non-implantable disposable or extracorporeal medical device or prosthesis or as an in vitro or in vivo diagnostic device, and wherein, when said polymer body comprises a membrane component in a diagnostic device, said component contains immuno-reactants.

5. The device or prosthesis of claim 1, wherein A and Z are methoxy ether-terminated polyethylene oxides having one or more crosslinkable reactive groups or groups capable of binding biologically-active molecules along the polyethyleneoxide chain.

6. The device or prosthesis of claim 1, wherein said polymeric composition of matter has a polyurethane hard block, a polyoxyalkylene soft block, and at least two surface-modifying amphipathic moieties, wherein at least one of said moieties is a surface active endgroup having a chain that bears multiple pendant groups of different polarity or composition than the main chain of the surface active endgroup.

7. The device or prosthesis of claim 1, wherein said polymeric composition of matter comprises a polyoxyalkylene chain having at least one surface-modifying amphipathic moiety, wherein said moiety is a surface active hydrophilic endgroup having a chain bearing multiple pendant hydrophobic groups, wherein the polyoxyalkylene polymer comprising the at least one surface-modifying amphipathic moiety has a molecular weight in the range 5000-5,000,000 daltons.

8. The device or prosthesis of claim 7, wherein said polymeric composition of matter has a plurality of acryloxy, methacryloxy, or other crosslinkable reactive groups along a polyethyleneoxide chain.

9. The device or prosthesis of claim 7, wherein said polymeric composition of matter has a plurality of amino, hydroxyl, carboxyl, or other groups capable of binding biologically-active molecules along a polyethyleneoxide chain.

* * * * *